United States Patent [19]

Oku et al.

[11] Patent Number: 5,789,405
[45] Date of Patent: Aug. 4, 1998

[54] OXASPIRO(2,5)OCTANE DERIVATIVE

[75] Inventors: Teruo Oku; Chiyoshi Kasahara; Takehiko Ohkawa; Masashi Hashimoto, all of Tsukuba, Japan

[73] Assignee: Fujisawa Pharmaceutical Co., Ltd., Osaka, Japan

[21] Appl. No.: 711,420

[22] Filed: Jun. 5, 1991

Related U.S. Application Data

[63] Continuation of Ser. No. 386,240, Jul. 28, 1989, abandoned.

[30] Foreign Application Priority Data

| Aug. 12, 1988 | [GB] | United Kingdom | 8819256.2 |
| Aug. 12, 1988 | [GB] | United Kingdom | 8819258.8 |
| Apr. 10, 1989 | [GB] | United Kingdom | 8908029.5 |
| Apr. 28, 1989 | [GB] | United Kingdom | 8909794.3 |

[51] Int. Cl.$^6$ .......... A61K 31/54; C07D 279/12; C07D 215/16; C07D 303/04
[52] U.S. Cl. .......... 514/227.8; 514/231.5; 514/255; 514/314; 514/326; 514/336; 514/422; 514/475; 544/59; 544/162; 544/170; 544/374; 546/153; 546/220; 546/269; 548/517; 549/332
[58] Field of Search .......... 549/332; 514/475, 514/227.8, 231.5, 255, 314, 326, 336, 422; 544/59, 162, 170, 374; 546/153, 220, 269; 548/517

[56] References Cited

FOREIGN PATENT DOCUMENTS

| 0354787 | 2/1990 | European Pat. Off. . |
| 0357061 | 3/1990 | European Pat. Off. . |
| 0359036 | 3/1990 | European Pat. Off. . |
| 0387650 | 9/1990 | European Pat. Off. . |
| 0000476 | 1/1987 | Japan . |
| 0007270 | 1/1991 | Japan . |

OTHER PUBLICATIONS

Chemical Abstracts, vol. 106, No. 23, Jun. 8, 1987, Columbus, Ohio, USA, Fujisawa Pharmaceutical Co. "Immunosuppressent manufacture by Penicillium species", p. 604, col. 2, Abstract No. 194 770b.

Chemical Abstracts, vol. 106, No. 21, May 25, 1987, Columbus, Ohio, USA; Fujisawa Pharmaceutical Co. "Oxaspirooctane compounds as immunosuppressants" p. 706, col. 2, Abstract No. 176 153y.

Chemical Abstracts, vol. 105, No. 7, Aug. 18, 1986, Columbus, Ohio, USA, Fujisawa Pharmaceutical Co. "Manufacture of immuno-suppressive FR-65814 with Penicillium jensenii" p. 515, col. 2, abstract No. 59 452p.

Tarbell, D S et al "The Structure of Fumagillin" JACS Communications to the Editor vol. 82 pp. 1005-1011 (1960).

*Primary Examiner*—C. Warren Ivy
*Assistant Examiner*—Taofiq A. Solola
*Attorney, Agent, or Firm*—Oblon, Spivak, McClelland, Maier & Neustadt, P.C.

[57] ABSTRACT

An oxaspiro [2,5]octane derivative of the formula:

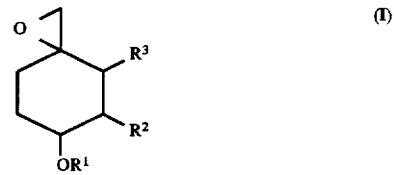

(I)

useful in inhibiting angiogenesis in solid tumors.

16 Claims, No Drawings

OXASPIRO(2,5)OCTANE DERIVATIVE

This application is a Continuation of application Ser. No. 07/386,240, filed on Jul. 28, 1989, now abandoned.

This invention relates to a new oxaspiro[2,5]octane derivative or salt thereof. More particularly, it relates to a new oxaspiro[2,5]octane derivative or salt thereof which has an angiogenesis inhibitory activity, and therefore is useful as an angiogenesis inhibitor, especially for the treatment of solid tumors, to processes for the preparation thereof and to a pharmaceutical composition comprising the same.

The oxaspiro[2,5]octane derivative of this invention can be represented by the following formula

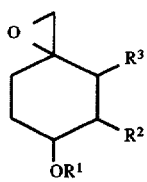
(I)

wherein
$R^1$ is carbamoyl;
  lower alkylcarbamoyl;
  hydroxy(lower)alkylcarbamoyl;
  lower alkoxy(lower)alkylcarbamoyl;
  lower alkylthio(lower)alkylcarbamoyl;
  lower alkoxycarbonyl(lower)alkylcarbamoyl;
  lower alkylcarbamoyloxy(lower)alkylcarbamoyl;
  di(lower)alkylcarbamoyl;
  N-[hydroxy(lower)alkyl](lower)alkylcarbamoyl;
  N-[hydroxy(lower)alkyl](lower)alkylcarbamoyloxy(lower)alkylcarbamoyl;
  lower alkylcarbamoyloxy(lower)alkenoyl;
  N-[heterocycliccarbonyloxy(lower)alkyl](lower)alkylcarbamoyl;
  cyclo(lower)alkylcarbamoyl;
  arylcarbamoyl;
  haloarylcarbamoyl;
  protected carbamoyl;
  lower alkylthiocarbamoyl;
  heterocycliccarbamoyl;
  ar(lower)alkenoyl;
  lower alkoxycarbonyl;
  heterocycliccarbonyl which may have lower alkyl, hydroxy, hydroxy(lower)alkyl, lower alkoxy(lower)alkyl or lower alkoxycarbonyl;
  lower alkyl;
  carboxy(lower)alkyl;
  protected carboxy(lower)alkyl;
  ar(lower)alkyl which may have halogen or lower alkoxy;
  heterocyclic(lower)alkyl;
  lower alkylcarbamoyl(lower)alkyl;
  hydroxy(lower)alkenoyl;
  acyloxy(lower)alkenoyl; or
  diacyloxy(lower)alkenoyl;
$R^2$ lower alkoxy and
$R^3$

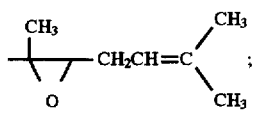
;

-continued

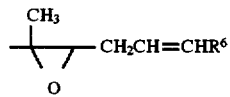

wherein $R^6$ is a protected carboxy;

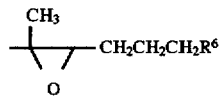

wherein $R^6$ is a protected carboxy;

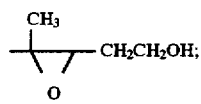

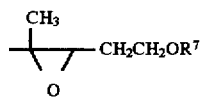

wherein $R^7$ is a protected carboxy(lower)alkyl or ar(lower)alkyl which may have halogen; or

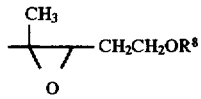

wherein $R^8$ is acyl.

The salts of the object compound (I) are preferably pharmaceutically acceptable salts thereof and may include a metal salt such as an alkali metal salt (e.g., sodium salt, potassium salt, etc.) and an alkaline earth metal salt (e.g., calcium salt, magnesium salt, etc.), ammonium salt, an organic amine salt (e.g., trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, toluenesulfonate, etc.), an inorganic acid salt (e.g., hydrochloride, hydrobromide, sulfate, phosphate, etc.), or a salt with an amino acid (e.g., arginine, aspartic acid, glutamic acid, etc.), and the like.

According to this invention, the object compound (I) and pharmaceutically acceptable salt thereof can be prepared by, for example, the following processes.

Process 1:

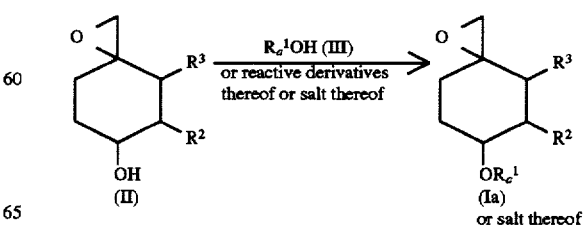

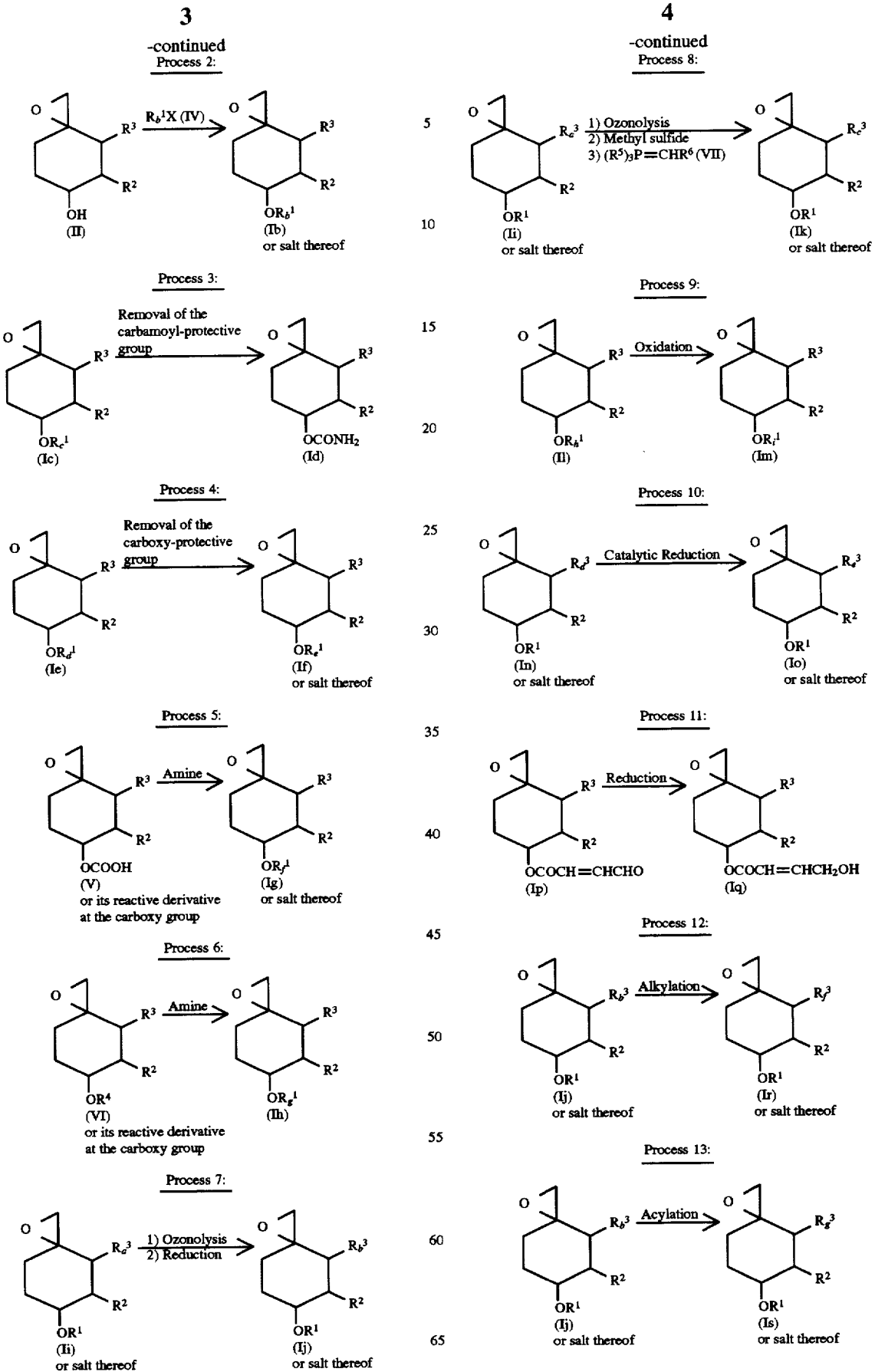

-continued

Process 14

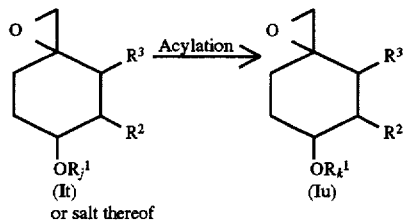

(It) or salt thereof → (Iu)

Process 15:

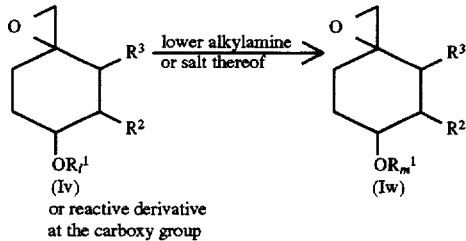

(Iv) or reactive derivative at the carboxy group → (Iw)

wherein
$R^1$, $R^2$ and $R^3$ are each as defined above.
$R_a^1$ is carbamoyl,
  lower alkylcarbamoyl,
  hydroxy(lower)alkylcarbamoyl,
  lower alkoxy (lower)alkylcarbamoyl,
  lower alkylthio (lower)alkylcarbamoyl,
  lower alkoxycarbonyl(lower)alkylcarbamoyl,
  lower alkylcarbamoyloxy(lower)alkylcarbamoyl,
  di(lower)alkylcarbamoyl,
  N-[hydroxy(lower)alkyl](lower)alkylcarbamoyl,
  N-[hydroxy(lower)alkyl](lower)alkylcarbamoyloxy(lower)alkylcarbamoyl,
  lower alkylcarbamoyloxy(lower)alkenoyl,
  N-[heterocycliccarbonyloxy(lower)alkyl](lower)alkylcarbamoyl, hydroxy(lower)alkenoyl,
  acyloxy(lower)alkenoyl, diacyloxy(lower)alkenoyl, cyclo(lower)alkylcarbamoyl, arylcarbamoyl, haloarylcarbamoyl, protected carbamoyl, lower alkylthiocarbamoyl, heterocycliccarbamoyl, ar(lower)alkenoyl, lower alkoxycarbonyl, heterocycliccarbonyl which may have lower alkyl, hydroxy, hydroxy(lower)alkyl, lower alkoxy(lower)alkyl or lower alkoxycarbonyl,
$R_b^1$ is lower alkyl;
  carboxy(lower)alkyl;
  protected carboxy(lower)alkyl;
  ar(lower)alkyl which may have halogen or lower alkoxy; or
  heterocyclic(lower)alkyl,
$R_c^1$ is a protected carbamoyl,
$R_d^1$ is a protected carboxy(lower)alkyl or a protected carboxy(lower)alkylcarbamoyl,
$R_e^1$ is carboxy(lower)alkyl,
X is acid residue,
$R_f^1$ is lower alkylcarbamoyl,
  hydroxy(lower)alkylcarbamoyl,
  lower alkoxy(lower)alkylcarbamoyl,
  lower alkylthio(lower)alkylcarbamoyl,
  lower alkoxycarbonyl(lower)alkylcarbamoyl,
  lower alkylcarbamoyloxy-(lower) alkylcarbamoyl,
  di(lower)alkylcarbamoyl,
  N-[hydroxy(lower)alkyl](lower)alkylcarbamoyl, cyclo(lower)alkylcarbamoyl,
arylcarbamoyl,
haloarylcarbamoyl,
protected carbamoyl,
morpholinocarbonyl,
morpholinocarbamoyl,
thiomorpholin-4-ylcarbonyl,
piperidinocarbonyl,
piperidinocarbamoyl,
hydroxypiperidinocarbonyl,
lower alkylpiperidinocarbonyl,
2-oxopyrrolidin-1-yl(lower)alkylcarbamoyl,
hydroxy(lower)alkylpyrrolidin-1-ylcarbonyl,
lower alkoxy(lower)alkylpyrrolidin-1-ylcarbonyl,
pyperazin-1-ylcarbonyl, or
lower alkoxycarbonylpiperazin-1-ylcarbonyl,
$R^4$ is hydroxycarbonyloxy(lower)alkylcarbamoyl,
  N-[hydroxycarbonyloxy(lower)alkyl](lower)alkylcarbamoyl or
  hydroxycarbonyloxypiperidinocarbonyl,
$R_g^1$ is lower alkylcarbamoyloxy(lower)alkylcarbamoyl,
  N-[hydroxy(lower)alkyl](lower)alkylcarbamoyloxy(lower)alkylcarbamoyl,
  lower alkylcarbamoyloxy(lower)alkenoyl,
  N-[thiomorpholin-4-ylcarbonyloxy(lower)alkyl](lower)alkylcarbamoyl,
  N-[morpholinocarbonyloxy(lower)alkyl](lower)alkylcarbamoyl or
  lower alkylcarbamoyloxypiperidinocarbonyl,
$R_a^3$ is

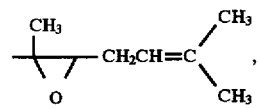

$R_b^3$ is

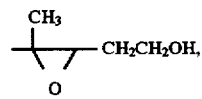

$R_c^3$ is

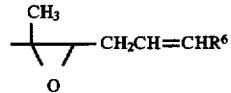

wherein $R^6$ is protected carboxy,
$R^5$ is aryl,
$R_h^1$ is thiomorpholin-4-ylcarbonyl or

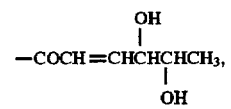

$R_i^1$ is 1-oxothiomorpholin-4-ylcarbonyl, 1,1-dioxothiomorpholin-4-ylcarbonyl or —COCH=CHCHO, $R_d^3$

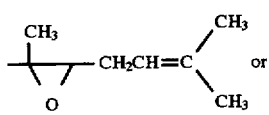

wherein $R^6$ is the same as defined above.

$R_e^3$ is

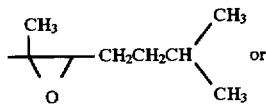

wherein $R^6$ is the same as defined above.

$R_f^3$ is

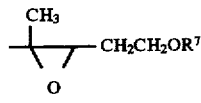

wherein $R^7$ is a protected carboxy(lower)alkyl, or ar(lower)alkyl which may have halogen.

$R_g^3$ is

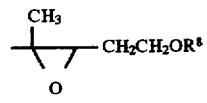

wherein $R^8$ is acyl.

$R_j^1$ is

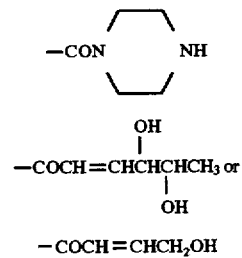

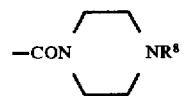

wherein $R^8$ is acyl.

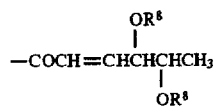

wherein $R^8$ is acyl or —COCH=CHCH$_2$OR$^8$ wherein $R^8$ is acyl.

$R_l^1$ is carboxy(lower)alkyl and $R_m^1$ is lower alkylcarbamoyl(lower)alkyl.

The starting compound (II) can be prepared in a conventional manner as, for example, that described in Journal of the American Chemical Society 94, 2549 (1972).

The starting compounds (III) and (IV) can also be prepared in a conventional manner as illustrated in working Examples mentioned below.

The salts of the compound (Ia), (Ib), (Ig) and (It) may include an inorganic or organic acid salt as those exemplified in the explanation of the salts of the object compound (I).

The salts of the compound (If) and (III) may include a metal salt, ammonium salt or an organic amine salt as those exemplified in the explanation of the salts of the object compound (I).

The salts of the compounds (Ii), (Ij), (Ik), (In), (Io), (Ir) and (Is) are the same salt as those exemplified in the explanation of the salts of the object compound (I).

In the above and subsequent descriptions of this specification, suitable examples and illustrations of the various definitions are explained in detail in the followings.

The term "lower" is intended to mean 1 to 6 carbon atom(s), unless otherwise indicated.

Suitable "lower alkyl" in the terms "lower alkylcarbamoyl", "hydroxy(lower)alkylcarbamoyl", "lower alkoxy(lower)alkylcarbamoyl", "lower alkylthio(lower) alkylcarbamoyl", "lower alkoxycarbonyl(lower) alkylcarbamoyl", "lower alkylcarbamoyloxy(lower) alkylcarbamoyl", "di(lower)alkylcarbamoyl", "ar(lower) alkyl", "N-[hydroxy(lower)alkyl](lower)alkylcarbamoyl", "N-[hydroxy(lower)alkyl](lower)alkylcarbamoyloxy (lower)alkylcarbamoyl", "lower alkylcarbamoyloxy(lower) alkenoyl", "N-[heterocycliccarbonyloxy(lower)alkyl] (lower)alkylcarbamoyl", "lower alkylthiocarbamoyl", "lower alkyl", "hydroxy(lower)alkyl", "lower alkoxy (lower)alkyl", "carboxy(lower)alkyl", "protected carboxy (lower)alkyl", "heterocyclic(lower)alkyl", "lower alkylcarbamoyl(lower)alkyl", "hydroxycarbonyloxy(lower) alkylcarbamoyl", "N-[hydroxycarbonyloxy(lower)alkyl] (lower)alkylcarbamoyl", "N-[thiomorpholin-4-ylcarbonyloxy(lower)alkyl](lower)alkylcarbamoyl", "N-[morpholinocarbonyloxy(lower)alkyl](lower) alkylcarbamoyl" and "lower alkylcarbamoyloxypiperidinocarbonyl" may include methyl, ethyl, propyl, isopropyl, butyl, isobutyl, t-butyl, pentyl, hexyl and the like.

Suitable "lower alkoxy" in the terms "lower alkoxy (lower)alkylcarbamoyl", "lower alkoxycarbonyl(lower) alkylcarbamoyl", "lower alkoxycarbonyl" and "lower alkoxy(lower)alkyl" may include methoxy, ethoxy, propoxy, butoxy, pentyloxy, hexyloxy and the like.

Suitable "lower alkylthio" in the term "lower alkylthio (lower)alkylcarbamoyl" may include methylthio, ethylthio, propylthio, butylthio, pentylthio and hexylthio.

Suitable "lower alkenoyl" in the term "lower alkylcarbamoyloxy(lower)alkenoyl", "hydroxy(lower) alkenoyl", "acyloxy(lower).alkenoyl" and "diacyloxy (lower)alkenoyl" and "ar(lower)alkenoyl" is C$_3$–C$_6$ alkenoyl such as acryloyl, crotonoyl and the like.

Suitable "cyclo(lower)alkylcarbamoyl" is "cyclo($C_3$–$C_7$) alkylcarbamoyl" and may include cyclopropylcarbamoyl, cyclobutylcarbamoyl, cyclopentylcarbamoyl, cyclohexylcarbamoyl, cycloheptylcarbamoyl and the like.

Suitable "aryl" in the terms "arylcarbamoyl", "haloarylcarbamoyl", "ar(lower)alkyl" and "ar(lower) alkenoyl" may include phenyl, tolyl, xylyl, naphthyl and the like.

Suitable "halogen" in the terms "haloaryl" and "halogen" may include chlorine, bromine, iodine and fluorine.

Suitable "heterocyclic" in the terms "N-[heterocycliccarbonyloxy(lower)alkyl](lower) alkylcarbamoyl", "heterocycliccarbonyl", "heterocycliccarbamoyl" and "heterocyclic(lower)alkyl" may include N-containing heteromonocyclic (e.g. pyridyl, pyrrolidyl, piperidyl, piperazinyl, 2-oxopyrrolidyl, etc.), N,O-containing heteromonocyclic (e.g. morpholinyl, etc.) N,S-containing heteromonocyclic (e.g. thiomorpholinyl, etc.), benzene-fused N-containing heterocyclic (e.g. quinolyl, etc.) and the like.

Suitable "protected carbamoyl" is carbamoyl protected by a conventional carbamoyl protective group such as trichloroacetyl and the like.

Suitable "protected carboxy" in the terms "protected carboxy(lower)alkyl" and "protected carboxy" may include an esterified carboxy such as lower alkoxy carbonyl (e.g. methoxycarbonyl, ethoxycarbonyl, propoxycarbonyl, isopropoxycarbonyl, butoxycarbonyl, pentyloxycarbonyl, hexyloxycarbonyl, etc.) and the like.

Suitable "acyl" in the terms "acyloxy(lower)alkenoyl", "diacyloxy(lower)alkenoyl" and "acyl" may include lower alkanoyl (e.g. formyl, acetyl, propionyl, etc.), aroyl (e.g. benzoyl, etc.) lower alkanesulfonyl (e.g. methanesulfonyl, ethanesulfonyl, etc.) and the like.

Suitable "acid residue" may include halogen (e.g. fluorine, bromine, iodine, chlorine, etc.).

The process as illustrated above and explained in more detail in the followings.

Process 1

The object compound (Ia) or salt thereof can be prepared by reacting the compound (II) with the compound (III) or reactive derivatives thereof or salt thereof.

The reactive derivatives of the compound (III) may include acid halide (e.g. acid chloride, etc.), acid anhydride, activated amide, activated ester, isocyanate (e.g. lower alkylisocyanate, cyclo(lower)alkylisocyanate, arylisocyanate, etc.) and the like.

The reaction is preferably conducted in the presence of an organic or inorganic base as those exemplified in the explanation of the Process 2.

This reaction is usually carried out in a solvent which does not adversely influence the reaction such as methanol, ethanol, propanol, tetrahydrofuran, chloroform and the like.

The reaction temperature is not critical and the reaction can be carried out under heating to under cooling.

Process 2

The object compound (Ib) or salt thereof can be prepared by reacting the compound (II) with the compound (IV).

This reaction is usually carried out in a solvent which does not adversely influence the reaction such as N,N-dimethylformamide, dimethylsulfoxide, tetrahydrofuran and the like.

The reaction can preferably be conducted in the presence of an organic or inorganic base such as alkali metal (e.g. sodium), alkaline earth metal (e.g. calcium), alkali or alkaline earth metal hydride (e.g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate), alkali or alkaline earth metal alkoxide (e.g. sodium ethoxide, lithium methoxide, magnesium methoxide), trialkylamine (e.g. triethylamine), pyridine, bicyclodiaza compound (e.g. 1,5-diazabicyclo[3,4,0] nonene-5,1,5-diazabicyclo[5,4,0]undecene-5, etc. and the like.

The reaction temperature is not critical and the reaction can be carried out under cooling to under heating.

Process 3: Compound (Ic)→Compound (Id)
Process 4: Compound (Ie)→Compound (If)

The compound (Id) or (If) can be prepared by subjecting the compound (Ic) or (Ie) to the removal reaction of the carbamoyl-(or carboxy-)protective group.

The removal reaction of this process may include hydrolysis, reduction and the like.

The hydrolysis is preferably carried out in the presence of inorganic or organic acid (e.g. hydrochloric acid, sulfuric acid, acetic acid, trifluoroacetic acid, etc.), or inorganic or organic base (e.g. sodium hydroxide, etc.).

The reaction of this process is usually carried out in a solvent which does not adversely influence the reaction such as water, methanol, ethanol, propanol, acetic acid and the like, at a temperature range of cooling to heating.

Process 5: Compound (III)→Compound (Ig)
Process 6: Compound (IV)→Compound (Ih)

The object compound (Ig) or (Ih) or salt thereof can be prepared by the compound (V) or (VI) or their reactive derivative at the carboxy group with an amine.

The reactive derivative at the carboxy group of the compound (V) and (VI) may include an aryl ester thereof (e.g. p-nitrophenyl ester, etc.) and the like.

The amine may include primary or secondary amine such as lower alkylamine, hydroxy(lower)alkylamine, lower alkylthio(lower)alkylamine, N-[hydroxy(lower)alkyl] (lower)alkylamine, lower alkoxy(lower)alkylamine, lower alkoxy(lower)alkylamine, morpholine, piperazine, lower alkoxycarbonylpiperazine, lower alkylpiperidine, thiomorpholine, aminopiperidine, 2-oxopyrrolidinyl(lower) alkylamine, aminomorpholine, hydroxypiperazine, hydroxy (lower)alkylpyrrolidine, lower alkoxy(lower) alkylpyrrolidine and the like.

This reaction is usually carried out in a solvent which does not adversely influence the reaction such as dichloromethane, chloroform, dimethylsulfoxide and the like.

The reaction temperature is not critical and the reaction can be carried out under heating to under cooling.

Process 7

The compound (Ij) or salt thereof can be prepared by subjecting the compound (Ii) or salt thereof to ozonolysis and then reducing the resultant compound.

The ozonolysis can be carried out in a conventional manner.

The reduction can be carried out by using a conventional reducing agent such as alkali metal borohydride (e.g. sodium borohydride) and the like.

These reaction is usually carried out in a solvent is which does not adversely influence the reaction such as methanol, dichloromethane, chloroform, dimethylsulfoxide and the like.

The reaction temperature is usually carried out under cooling.

Process 8

The compound (Ik) or salt thereof can be prepared by subjecting the compound (Ii) or salt thereof to ozonolysis and then treating the resultant compound with methyl sulfide and then reacting the resultant compound with the compound (VII).

The ozonolysis and subsequent treatment with methyl sulfide can be carried out in a conventional manner.

These reaction can be carried out in a solvent which does not adversely influence the reaction such as dichloromethane under cooling.

The last reaction is usually carried out in a solvent which does not adversely influence the reaction under heating to under cooling.

Process 9

The compound (Im) can be prepared by oxiding the compound (Il).

The oxidation is usually carried out by using a conventional oxidizing agent (e.g. sodium periodide, haloperbenzoic acid etc.) in a solvent which does not adversely influence the reaction such as water, dioxane, dichloromethane, methanol and the like under cooling.

Process 10

The compound (Io) or salt thereof can be carried out by subjecting the compound (In) or salt thereof to the catalytic reduction.

The catalytic reduction can be carried out by using a conventional catalyst (e.g. $PtO_2$) in a solvent which does not adversely influence the reaction such as ethyl acetate and the like at ambient temperature.

Process 11

The compound (Iq) can be prepared by reducing the compound (Ip).

The reduction is usually carried out by using a conventional reducing agent such as alkali metal borohydride (e.g. sodium borohydride) in a solvent which does not adversely influence the reaction such as water, methanol, dimethylformamide and the like under cooling to heating.

Process 12

The compound (Ir) can be prepared by reacting the compound (Ij) with an alkylating agent.

The alkylating agent may include ar(lower)alkyl halide (e.g. benzyl bromide, etc.) and lower alkyl halo(lower) alkanate (e.g. ethyl bromoacetate, etc.) and the like.

This reaction is usually carried out in a solvent such as toluene, dimethylformamide and the like under mild condition.

Process 13: Compound (Ij)→Compound (Is)
Process 14: Compound (It)→Compound (Iu)

The compound (Is), (Iu) or salt thereof can be prepared by reacting the compound (Ij), (It) or salt thereof with an acylating agent.

The acylating agent is represented by the formula: $R^8OH$ (VIII) wherein $R^8$ is acyl or reactive derivative thereof or salt thereof. The reactive derivative of the compound (VIII) is the same as those exemplified in the explanation of that of the compound (III).

This acylation is carried out under the same condition as that of Process 1.

Process 15

The compound (Iw) can be prepared by reacting the compound (Iv) or reactive derivative at the carboxy group with lower alkylamine.

The lower alkylamine may include methylamine, ethylamine, propylamine and the like. The reactive derivative of the compound (Iv) may include acid halide and the like.

The reaction conditions of this process is the same as those of Process 1.

The object compound of the above processes can be isolated and purified in a conventional manner.

The object compound (I) of this invention has an angiogenesis inhibitory activity and therefore is useful for the treatment of solid tumor, rheumatoid arthritis, diabetic retinopathy, psoriasis and the like.

The following test is given for the purpose of illustrating angiogenesis inhibitory activity of the object compound (I). Test effect of the object compound (I) on endothelial cell growth Endothelial cells from human umbilical vein (HUVEC) were used for this experiment.

HUVEC ($2 \times 10^3$ cells per well) were plated on 96 wells microtiter plates previously coated with human fibronectin and incubated with MCDB 151 [GIBCO] medium supplemented with 15% FBS (fetal bovine serum), 100% µg/ml ECGS (Endothelial cell growth supplement), 10 µg/ml heparin in the presence of the test compound at 37° C. under 5% $CO_2$ in the air for 5 days. At the end of the experiments, the growth rate of HUVEC was measured according to the MTT method [Cancer treatment Reports 71, 1141–1149 (1987)].

The test compound inhibited the proliferation of human umbilical endothelial cells.

$IC_{50}$ values [50% inhibition doses of the test compound to endothelial cell growth) of the test compound were graphically determined and are shown in the following table.

| Test Compound | $IC_{50}$ (µg/ml) |
|---|---|
| structure with OCONHCH₃ | $2.1 \times 10^{-4}$ |
| structure with OCON(morpholine) | $6.2 \times 10^{-4}$ |

The object compound (I) of this invention in admixture with pharmaceutically acceptable carriers can orally or parenterally be administered as antitumor agent to mammals including human being in a form of a pharmaceutical composition such as capsules, tablets, granules, powders, buccal tablets, sublingual tablets, and solutions.

The pharmaceutically acceptable carriers may include various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disentegrator (e.g. starch, carboxymethyl cellulose, calcium salt of carboxymethyl cellulose, hydroxypropyl-starch, sodium glycole-starch, sodium bicarbonate, calcium phosphate, calcium citrate, etc.), lubricant (e.g. magnesium stearate aerosil, talc, sodium laurylsulfate, etc.), flavoring agent (e.g. citric acid, mentol, glycine, organge powders, etc.), preservative (sodium benzoate, sodium bisulfite, methylparaben, propylparaben, etc.), stabilizer (citric acid, sodium citrate, acetic acid, etc.), suspending agent (e.g.

methyl cellulose, polyvinylpyrrolidone, aluminum stearate, etc.), dispersing agent [e.g. surface active agent, etc.], aqueous diluting agent (e.g. water), oils (e.g. sesame oil, etc.), base wax (e.g. cacao butter, polyethyleneglycol, white petrolatum, etc.).

A dosage of the object compound (I) is to be varied depending on various factors such as kind of diseases, weight and/or age of a patient, and further the kind of administration route.

The preferred dosage of the object compound (I) is usually selected from a dose range of 0.01–10 mg/kg/day in the case of injection and 0.5–50 mg/kg/day in the case of oral administration.

The following Examples are given for the purpose of illustrating this invention.

EXAMPLE 1

To a solution of 6-hydroxy-5-methoxy-4-[2-methyl-3-(3-methyl-2-butenyl)oxiranyl]-1-oxaspiro[2,5]octane (14.8 mg) in freshly distilled tetrahydrofuran (0.5 ml) was added sodium hydride (2.5 mg) in one portion at 5° C. The mixture was stirred for half an hour at the same temperature and then methyl isocyanate (6 µl) was added thereto. After stirring at ambient temperature for 1.5 hours, the mixture was treated with methyl isocyanate (6 µl) to complete the reaction.

The reaction mixture was stirred for 3.25 hours at ambient temperature and diluted with diethyl ether. The organic layer was washed with brine, dried, and concentrated to give a crude oil which was purified by preparative thin layer column chromatography to yield 6-methylcarbamoyloxy-5-methoxy-4-[2-methyl-3-(3-methyl-2-butenyl)oxiranyl]-1-oxaspiro[2,5]octane (11 mg) as crystals.

mp: 92°–93° C.

IR (CHCl$_3$): 3460, 3360, 1715 cm$^{-1}$

NMR (CDCl$_3$, δ): 1.0–1.15 (1H, m), 1.20 (3H, s), 1.66 (3H, s), 1.73 (3H, s), 1.65–2.54 (6H, m), 2.54 (1H, d, J=5 Hz), 2.55 (1H, t, J=6 Hz), 2.79 (3H, d, J=5 Hz), 2.97 (1H, d, J=5 Hz), 3.47 (3H, s), 3.64 (1H, dd, J=11 Hz and 3 Hz), 4.75 (1H, br s), 5.20 (1H, t, J=8 Hz), 5.50 (1H, br s)

EXAMPLE 2

The following compounds were prepared in a similar manner to that of Example 1.

(1) 5-Methoxy-4-[2-methyl-3-(3-methyl-2-butenyl) oxiranyl]-6-phenylcarbamoyloxy-1-oxaspiro[2,5] octane Oil IR (CHCl$_3$): 1720, 1600, 1520, 1440, 1380, 1200, 1100 cm$^{-1}$ NMR (CDCl$_3$, δ) : 1.04–1.16 (1H, m), 1.24 (3H, s), 1.66 (3H, s), 1.75 (3H, s), 1.74–2.50 (6H, m), 2.58 (1H, d, J=4 Hz), 2.62 (1H, t, J=7 Hz), 3.01 (1H, d, J=4 Hz), 3.48 (3H, s), 3.72 (1H, dd, J=10 Hz and 3 Hz), 5.22 (1H, m), 5.56 (1H, m), 6.80 (1H, s), 7.05–7.45 (5H, m)

(2) 6-Ethylcarbamoyloxy-5-methoxy-4-[2-methyl-3-(3-methyl-2-butenyl)oxiranyl]-1-oxaspiro[2,5]octane mp: 65° C.

IR (CHCl$_3$): 3450, 1705 cm$^{-1}$

NMR (CDCl$_3$, δ) : 0.99–1.30 (1H, m), 1.14 (3H, t, J=8 Hz), 1.22 (3H, s), 1.67 (3H, s), 1.75 (3H, s), 1.78–2.48 (6H, m), 2.56 (1H, d, J=4 Hz), 2.58 (1H, t, J=5 Hz), 2.99 (1H, d, J=4 Hz), 3.22 (2H, m), 3.45 (3H, s), 3.64 (1H, dd, J=2 Hz and 12 Hz), 4.75 (1H, br s), 5.21 (1H, t, J=7 Hz), 5.50 (1H, br s)

(3) 6-Isopropylcarbamoyloxy-5-methoxy-4-[2-methyl-3-(3-methyl-2-butenyl)oxiranyl]-1-oxaspiro[2,5]octane Oil IR (CHCl$_3$): 3430, 1700 cm$^{-1}$ NMR (CDCl$_3$, δ): 1.00–1.23 (1H, m), 1.17 (6H, d, J=6 Hz), 1.22 (3H, s), 1.66 (3H, s), 1.75 (3H, s), 1.78–2.48 (6H, m), 2.54 (1H, d, J=4 Hz), 2.57 (1H, t, J=5 Hz), 2.98 (1H, d, J=4 Hz), 3.45 (3H, s), 3.65 (1H, dd, J=2 Hz and 12 Hz), 3.80 (1H, m), 4.61 (1H, d, J=7 Hz), 5.21 (1H, t, J=7 Hz), 5.48 (1H, s)

(4) 6-Cyclohexylcarbamoyloxy-5-methoxy-4-[2-methyl-3-(3-methyl-2-butenyl)oxiranyl]-1-oxaspiro[2,5]octane mp: 61° C.

IR (CHCl$_3$): 3440, 1700 cm$^{-1}$

NMR (CDCl$_3$, δ) 0.99–2.49 (18H, m), 1.22 (3H, s), 1.66 (3H, s), 1.75 (3H, s), 2.55 (1H, d, J=4 Hz), 2.57 (1H, t, J=5 Hz), 2.97 (1H, d, J=4 Hz), 3.45 (3H, s), 3.65 (1H, dd, J=2 Hz and 12 Hz), 4.69 (1H, d, J=8 Hz), 5.22 (1H, t, J=7 Hz), 5.46 (1H, s)

(5) 6-(4-Chlorophenylcarbamoyloxy)-5-methoxy-4-[2-methyl-3-(3-methyl-2-butenyl)oxiranyl]-1-oxaspiro[2,5] octane mp: 63°–66° C.

IR (CHCl$_3$) 3430, 1720 cm$^{-1}$

NMR (CDCl$_3$, δ) 1.04–1.18 (1H, m), 1.24 (3H, s), 1.68 (3H, s), 1.76 (3H, s), 1.83–2.50 (6H, m), 2.58 (1H, d, J=4 Hz), 2.61 (1H, t, J=5 Hz), 3.01 (1H, d, J=4 Hz), 3.47 (3H, s), 3.72 (1H, dd, J=2 Hz and 12 Hz), 5.22(1H, t, J=7 Hz), 5.58 (1H, br s), 6.88 (1H, br s), 7.21–7.42 (4H, m)

(6) 5-Methoxy-4-[2-methyl-3-(3-methyl-2-butenyl) oxiranyl]-6-(trichloroacetylcarbamoyloxy)-1-oxaspiro[2,5]-octane Oil IR (CHCl$_3$): 3400, 1800, 1740 cm$^{-1}$ NMR (CDCl$_3$, δ): 1.10–1.20 (1H, m), 1.21 (3H, s), 1.65 (3H, s), 1.74 (3H, s), 1.85–2.49 (6H, m), 2.58 (1H, d, J=4 Hz), 2.62 (1H, t, J=5 Hz), 3.00 (1H, d, J=4 Hz), 3.50 (3H, s), 3.74 (1H, dd, J=12 Hz and 2 Hz), 5.19 (1H, t, J=7 Hz), 5.68 (1H, br s), 8.87 (1H, br s)

(7) 6-Propylcarbamoyloxy-5-methoxy-4-[2-methyl-3-(3-methyl- 2-butenyl)oxiranyl]-1-oxaspiro[2,5]octane mp: 87°–88° C.

IR (CHCl$_3$): 3450, 1750, 1510, 1230, 1125, 1100 cm$^{-1}$

NMR (CDCl$_3$, δ) 0.93 (3H, t, J=8 Hz), 1.00–1.13 (1H, m), 1.21 (3H, s), 1.52 (2H, m), 1.68 (3H, s), 1.75 (3H, s), 1.80–2.48 (6H, m), 2.52 (1H, d, J=4 Hz), 2.58 (1H, t, J=6 Hz), 3.14 (2H, q, J=7 Hz), 3.46 (3H, s), 3.65 (1H, dd, J=3 Hz and 11 Hz), 4.80 (1H, br s), 5.20 (1H, br t, J=7 Hz), 5.45 (1H, br s)

(8) 6-(Butylcarbamoyloxy)-5-methoxy-4-[2-methyl-3-(3-methyl-2-butenyl)oxiranyl]-1-oxaspiro[2,5]octane mp: 68°–69° C.

IR (CHCl$_3$): 3450, 1710, 1510, 1240, 1130, 1100 cm$^{-1}$

NMR (CDCl$_3$, δ): 0.93 (3H, t, J=8 Hz), 1.00–1.12 (1H, m), 1.22 (3H, s), 1.22–1.58 (4H, m), 1.57 (3H, s), 1.75 (3H, s), 1.75–2.45 (6H, m), 2.52 (1H, d, J=4 Hz), 2.54 (1H, t, J=6 Hz), 2.95 (1H, d, J=4 Hz), 3.14 (2H, q, J=7 Hz), 3.45 (3H, s), 3.63 (1H, dd, J=3 Hz and 11 Hz), 4.75 (1H, br s), 5.19 (1H, br t, J=7 Hz), 5.50 (1H, br s)

(9) 6-Ethylthiocarbamoyloxy-5-methoxy-4-[2-methyl-3-(3-methyl-2-butenyl)oxiranyl]-1-oxaspiro[2,5]octane mp: 83°–84° C.

IR (Nujol): 3300, 1535, 1190 cm$^{-1}$

NMR (CDCl$_3$, δ): 0.98–1.14 (1H, m), 1.22 (3H, s), 1.66 (3H, s), 1.75 (3H, s), 1.22 (3H, t, J=6 Hz), 1.78–2.50 (6H, m), 2.56 (1H, d, J=4 Hz), 2.58 (1H, t, J=6 Hz), 2.99 (1H, d, J=4 Hz), 3.45 (3H, s), 3.56 (2H, qd, J=5 Hz and 6 Hz), 3.72 (1H, dd, J=2 Hz and 12 Hz), 5.21 (1H, br t, J=7 Hz), 6.12 (1H, br s), 6.38–6.51 (1H, br s)

EXAMPLE 3

A solution of 5-methoxy-4-[2-methyl-3-(3-methyl-2-butenyl)oxiranyl]-6-(trichloroacetylcarbamoyloxy)-1-oxaspiro[2.5]octane (26 mg) and triethylamine (9.9 μl) in a mixture of water (0.8 ml) and ethanol (0.8 ml) was stirred overnight at ambient temperature. The mixture was diluted with diethyl ether and washed with brine. The mixture was dried and evaporated to yield 6-carbamoyloxy-5-methoxy-4-[2-methyl-3-(3-methyl-2-butenyl)oxiranyl]-1-oxaspiro[2.5]octane (18.2 mg) as white solids.

mp: 125°–126° C.

IR (CHCl$_3$): 3300, 1720 cm$^{-1}$

NMR (CDCl$_3$, δ): 1.10–1.20 (2H, m), 1.21 (3H, s), 1.66 (3H, s), 1.75 (3H, s), 1.85–2.48 (7H, m), 2.58 (1H, d, J=4 Hz), 2.62 (1H, t, J=5 Hz), 3.00 (1H, d, J=4 Hz), 3.50 (3H, s), 3.74 (1H, dd, J=12 Hz and 2 Hz), 4.91 (1H, br s), 5.20 (1H, t, J=7 Hz), 5.45 (1H, br s)

EXAMPLE 4

To a solution of 6-hydroxy-5-methoxy-4-[2-methyl-3-(3-methyl-2-butenyl)oxiranyl]-1-oxaspiro[2.5]octane (14.1 mg) in freshly distilled tetrahydrofuran (0.5 ml) was added sodium hydride (2.0 mg, 60% oil dispersion) in one portion at 5° C. The mixture was stirred for half an hour at the same temperature and then morpholinocarbonyl chloride (6.8 mg) was added thereto. The reaction mixture was stirred for 2 hours at ambient temperature and diluted with diethyl ether (2 ml). The organic layer was washed with water, dried and concentrated under reduced pressure. The residue was purified by column chromatography on silica gel (elution by diethyl ether/n-hexane=2/1) to yield 5-methoxy-4-[2-methyl-3-(3-methyl-2-butenyl)oxiranyl]-6-(morpholinocarbonyloxy)-1-oxaspiro[2.5]octane (9.7 mg) as an oil.

IR (CHCl$_3$): 1690, 1430, 1205 cm$^{-1}$

NMR (CDCl$_3$, δ): 1.05–1.17 (1H, m), 1.20 (3H, s), 1.57 (3H, s), 1.73 (3H, s), 1.79–2.46 (6H, m), 2.54 (1H, d, J=4 Hz), 2.60 (1H, t, J=6 Hz), 3.00 (1H, d, J=4 Hz), 3.47 (3H, s), 3.36–3.58 and 3.58–3.75 (9H, m), 5.22 (1H, m), 5.58 (1H, m)

EXAMPLE 5

The following compounds were prepared in a similar manner to that of Example 4.

(1) 6-Cinnamoyloxy-5-methoxy-4-[2-methyl-3-(3-methyl-2-butenyl)oxiranyl]-1-oxaspiro[2.5]octane Oil IR (CHCl$_3$): 1700, 1635, 1445, 1310, 1170 cm$^{-1}$ NMR (CDCl$_3$, δ) 1.06–1.20 (1H, m), 1.25 (3H, s), 1.58 (3H, s), 1.76 (3H, s), 1.85–2.50 (6H, m), 2.48 (1H, d, J=4 Hz), 2.62 (1H, t, J=6 Hz), 3.02 (1H, d, J=4 Hz), 3.48 (3H, s), 3.72 (1H, dd, J=10 Hz and 3 Hz), 5.22 (1H, m), 5.77 (1H, m), 6.50 (1H, d, J=15 Hz), 7.33–7.58 (5H, m), 7.68 (1H, d, J=15 Hz)

(2) 6-Cyclohexanoyloxy-5-methoxy-4-[2-methyl-3-(3-methyl-2-butenyl)oxiranyl]-1-oxaspiro[2.5]octane Oil IR (CHCl$_3$): 1720, 1405, 1375, 1170, 1130, 1100 cm$^{-1}$ NMR (CDCl$_3$, δ) 1.00–1.14 (1H, m), 1.20 (3H, s), 1.20–2.25 (15H, m), 1.65 (3H, s), 1.72 (3H, s), 2.25–2.47 (2H, m), 2.55 (1H, d, J=4 Hz), 2.60 (1H, t, J=6 Hz), 2.98 (1H, d, J=4 Hz), 3.40 (3H, s), 3.63 (1H, dd, J=3 Hz and 11 Hz), 5.20 (1H, br t, J=8 Hz), 5.62 (1H, m)

(3) 6-Dimethylcarbamoyloxy-5-methoxy-4-[2-methyl-3-(3-methyl- 2-butenyl)oxiranyl]-1-oxaspiro[2.5]octane.

Oil

IR (CHCl$_3$): 1680, 1480, 1440, 1395, 1375, 1180 cm$^{-1}$

NMR (CDCl$_3$, δ): 1.00–1.18 (1H, m), 1.22 (3H, s), 1.65 (3H, s), 1.75 (3H, s), 1.80–2.46 (6H, m), 2.53 (1H, d, J=4 Hz), 2.58 (1H, d, J=6 Hz), 2.90 (6H, s), 3.00 (1H, d, J=4 Hz), 3.46 (3H, s), 3.63 (1H, dd, J=3 Hz and 11 Hz), 5.22 (1H, t, J=8 Hz), 5.57 (1H, br s)

EXAMPLE 6

To a solution of 6-hydroxy-5-methoxy-4-[2-methyl-3-(3-methyl-2-butenyl)oxiranyl]-1-oxaspiro[2.5]octane (14.1 mg) in freshly distilled tetrahydrofuran (0.5 ml) was added sodium hydride (6.0 mg, 60% oil dispersion) in one portion at 5° C. The mixture was stirred for half an hour at the same temperature and then isobutyl chloroformate (7 mg) was added thereto. The reaction mixture was stirred for 2 hours at ambient temperature and then diluted with diethyl ether. The organic layer was washed with brine, dried, and concentrated under reduced pressure. The residue was purified by column chromatography on silica gel (elution by diethyl ether/n-hexane=1/3) to yield 6-isobutoxycarbonyloxy-5-methoxy-4-[2-methyl-3-(3-methyl-2-butenyl)oxiranyl]-1-oxaspiro[2.5]octane (5.1 mg) as an oil.

IR (CHCl$_3$) 1730, 1440, 1375, 1260, 1100 cm$^{-1}$

NMR (CDCl$_3$, δ): 0.94 (6H, d, J=6 Hz), 1.00–1.13 (1H, m), 1.20 (3H, s), 1.63 (3H, s), 1.73 (3H, s), 1.80–2.45 (7H, m), 2.52 (1H, d, J=4 Hz), 2.55 (1H, t, J=6 Hz), 2.95 (1H, d, J=4 Hz), 3.45 (3H, s), 3.63 (1H, dd, J=7 Hz and 11 Hz), 3.90 (2H, m), 5.19 (1H, br t, J=8 Hz), 5.45 (1H, br s)

EXAMPLE 7

To a solution of 6-hydroxy-5-methoxy-4-[2-methyl-3-(3-methyl-2-butenyl)oxiranyl]-1-oxaspiro[2.5]octane (14.1 mg) in freshly distilled tetrahydrofuran (0.5 ml) was added sodium hydride (60% oil dispersion, 2.0 mg) in one portion in an ice bath. The suspension was stirred for half an hour at the same temperature and thereto iodomethane (71 mg) was added. After stirring for 2 hours at ambient temperature, the mixture was diluted with diethyl ether and washed with water. The organic layer was dried and evaporated to give a crude oil which was purified by column chromatography on silica gel eluted by a mixture of diethyl ether and n-hexane (1:2) to yield 5,6-dimethoxy-4-[2-methyl-3-(3-methyl-2-butenyl)oxiranyl]-1-oxaspiro[2.5]octane (14.2 mg) as an oil.

IR (CHCl$_3$): 1440, 1380, 1105 cm$^{-1}$

NMR (CDCl$_3$, δ): 0.93–1.07 (1H, m), 1.20 (3H, s), 1.63 (3H, s), 1.72 (3H, s), 1.93–2.45 (6H, m), 2.51 (1H, d, J=4 Hz), 2.56 (1H, t, J=6 Hz), 2.95 (1H, d, J=4 Hz), 3.42 (3H, s), 3.46 (3H, s), 3.59 (1H, dd, J=3 Hz and 10 Hz), 3.92 (1H, m), 5.19 (1H, m)

EXAMPLE 8

The following compounds were prepared in a similar manner to that of Example 7.

(1) 6-Benzyloxy-5-methoxy-4-[2-methyl-3-(3-methyl-2-butenyl)oxiranyl)-1-oxaspiro[2.5]octane Oil IR (CHCl$_3$): 1450, 1380 cm$^{-1}$ NMR (CDCl$_3$, δ): 0.95–1.10 (1H, m), 1.22 (3H, s), 1.67 (3H, s), 1.74 (3H, s), 1.55–2.48 (6H, m), 2.53 (1H, d, J=5 Hz), 2.58 (1H, t, J=6 Hz), 2.96 (1H, d, J=5 Hz), 3.41 (3H, s), 3.58 (1H, dd, J=11 Hz and 2 Hz), 4.10 (1H, m), 4.70 (2H, ABq, J=12 Hz), 5.22 (1H, t, J=7.5 Hz), 7.28–7.45 (5H, m)

(2) 5-Methoxy-4-[2-methyl-3-(3-methyl-2-butenyl)oxiranyl]-6-(2-pyridylmethoxy)-1-oxaspiro[2.5]octane Oil IR (CHCl$_3$): 1590, 1430, 1370, 1105 cm$^{-1}$ NMR (CDCl$_3$, δ) 0.96–1.10 (1H, m), 1.23 (3H, s), 1.66 (3H, s), 1.75 (3H, s), 2.01–2.46 (6H, m), 2.52 (1H, d, J=4 Hz), 2.60 (1H, t, J=7 Hz), 3.97 (1H, d, J=4 Hz), 3.43 (3H, s), 3.62 (1H, dd, J=3 Hz and 10 Hz), 4.18 (1H, m), 4.75 (1H, d, J=13 Hz), 4.85 (1H, d, J=13 Hz), 5.22 (1H, m), 7.16 (1H, m), 7.55–7.72 (2H, m), 8.52 (1H, m)

(3) 5-Methoxy-4-[2-methyl-3-(3-methyl-2-butenyl)oxiranyl]-6-(2-quinolylmethoxy)-1-oxaspiro[2,5]octane mp: 82°–83° C.

IR (CHCl$_3$): 1420, 1375, 1200, 1100 cm$^{-1}$

NMR (CDCl$_3$, δ): 0.97–1.12 (1H, m), 1.22 (3H, s), 1.68 (3H, s), 1.75 (3H, s), 2.02–2.48 (6H, m), 2.55 (1H, d, J=4 Hz), 2.62 (1H, t, J=6 Hz), 2.99 (1H, d, J=4 Hz), 3.45 (3H, s), 3.65 (1H, dd, J=3 Hz and 11 Hz), 4.22 (1H, br s), 4.98 (2H, s), 5.24 (1H, m), 7.53 (1H, t, J=8 Hz), 7.72 (1H, t, J=8 Hz), 7.80 (1H, d, J=8 Hz), 7.84 (1H, d, J=8 Hz), 8.05 (1H, d, J=8 Hz), 8.18 (1H, d, J=8 Hz)

(4) 6-(4-Chlorobenzyloxy)-5-methoxy-4-[2-methyl-3-(3-methyl-2-butenyl)oxiranyl]-1-oxaspiro[2,5]octane Oil IR (CHCl$_3$) 1680, 1485, 1440, 1380, 1200 cm$^{-1}$ NMR (CDCl$_3$, δ): 0.95–1.10 (1H, m), 1.21 (3H, s), 1.68 (3H, s), 1.74 (3H, s), 1.90–2.46 (6H, m), 2.52 (1H, d, J=4 Hz), 2.56 (1H, t, J=6 Hz), 2.96 (1H, d, J=4 Hz), 3.41 (3H, s), 3.58 (1H, dd, J=3 Hz and 10 Hz), 4.08 (1H, br s), 4.60 (1H, d, J=10 Hz), 4.71 (1H, d, J=10 Hz), 5.20 (1H, br t, J=5 Hz), 7.30 (4H, s)

(5) 5-Methoxy-6-(4-methoxybenzyloxy)-4-[2-methyl-3-(3-methyl-2-butenyl)oxiranyl]-1-oxaspiro[2,5]octane Oil IR (CHCl$_3$): 1605, 1505, 1440, 1375, 1300, 1240, 1205 cm$^{-1}$ NMR (CDCl$_3$, δ): 0.91–1.08 (1H, m), 1.20 (3H, s), 1.62 (3H, s), 1.72 (3H, s), 1.88–2.44 (6H, m), 2.49 (1H, d, J=4 Hz), 2.53 (1H, t, J=6 Hz), 2.95 (1H, d, J=4 Hz), 3.38 (3H, s), 3.56 (1H, dd, J=3 Hz and 10 Hz), 3.32 (3H, s), 4.07 (1H, br s), 4.55 (1H, d, J=11 Hz), 4.65 (1H, d, J=11 Hz), 5.20 (1H, br t, J=5 Hz), 6.86 (2H, d, J=6 Hz), 7.30 (2H, d, J=6 Hz)

(6) 5-Methoxy-4-[2-methyl-3-(3-methyl-2-butenyl)oxiranyl]-6-(2-naphthylmethoxy)-1-oxaspiro[2,5]octane Oil IR (CHCl$_3$): 1440, 1370, 1220, 1100 cm$^{-1}$ NMR (CDCl$_3$, δ): 0.95–1.08 (1H, m), 1.21 (3H, s), 1.65 (3H, s), 1.75 (3H, s), 1.92–2.45 (6H, m), 2.52 (1H, d, J=4 Hz), 2.58 (1H, t, J=6 Hz), 2.95 (1H, d, J=4 Hz), 3.42 (3H, s), 3.59 (1H, dd, J=3 Hz and 10 Hz), 4.14 (1H, br t, J=8 Hz), 4.78 (1H, d, J=13 Hz), 4.88 (1H, d, J=13 Hz), 7.35–7.66 (3H, m), 7.75–7.90 (4H, m)

(7) 5-Methoxy-4-[2-methyl-3-(3-methyl-2-butenyl)oxiranyl]-6-(1-naphthylmethoxy)-1-oxaspiro[2,5]octane Oil IR (CHCl$_3$): 1370, 1100 cm$^{-1}$ NMR (CDCl$_3$, δ) 0.88–1.04 (1H, m), 1.22 (3H, s), 1.66 (3H, s), 1.72 (3H, s), 1.82–2.47 (6H, m), 2.49 (1H, d, J=4 Hz), 2.58 (1H, t, J=5 Hz), 2.93 (1H, d, J=4 Hz), 3.42 (3H, s), 3.60 (1H, dd, J=2 Hz and 12 Hz), 4.22 (1H, br s), 5.03 (1H, d, J=12 Hz), 5.22 (1H, br t, J=7 Hz), 5.30 (1H, d, J=12 Hz), 7.32–7.60 (4H, m), 7.22–7.90 (2H, m), 8.18–8.27 (1H, m)

(8) 6-Ethoxycarbonylmethoxy-5-methoxy-4-[2-methyl-3-(3-methyl-2-butenyl)oxiranyl]-1-oxaspiro[2,5]octane Oil IR (CHCl$_3$): 1740, 1440, 1380, 1130 cm$^{-1}$ NMR (CDCl$_3$, δ): 0.95–1.10 (1H, m), 1.22 (3H, s), 1.28 (3H, t, J=7 Hz), 1.66 (3H, s), 1.72 (3H, s), 2.02–2.48 (6H, m), 2.52 (1H, d, J=4 Hz), 2.58 (1H, t, J=6 Hz), 2.95 (1H, d, J=4 Hz), 3.48 (3H, s), 3.60 (1H, dd, J=10 Hz and 3 Hz), 4.20 (3H, m), 4.25 (1H, d, J=16 Hz), 4.48 (1H, d, J=16 Hz), 5.20 (1H, m)

EXAMPLE 9

A mixture of 6-ethoxycarbonylmethoxy-5-methoxy-4-[2-methyl-3-(3-methyl-2-butenyl)oxiranyl]-1-oxaspiro[2,5]-octane (17 mg) and 1N aqueous sodium hydroxide solution (0.09 ml) in ethanol (0.2 ml) was stirred for one hour at ambient temperature. The solution was neutralized with 1N hydrochloric acid and the separated oil was extracted with diethyl ether. The solvent was dried and concentrated in vacuo to yield 6-carboxymethoxy-5-methoxy-4-[2-methyl-3-(3-methyl-2-butenyl)oxiranyl]-1-oxaspiro-[2,5]octane (14.4 mg) as an oil.

IR (CHCl$_3$): 3400, 1760, 1440, 1370, 1120 cm$^{-1}$

NMR (CDCl$_3$, δ): 0.96–1.10 (1H, m), 1.22 (3H, s), 1.65 (3H, s), 1.72 (3H, s), 1.77–2.46 (6H, m), 2.46 (1H, d, J=4 Hz), 2.62 (1H, t, J=6 Hz), 2.95 (1H, d, J=4 Hz), 3.56 (3H, s), 3.70 (1H, dd, J=10 Hz and 3 Hz), 3.95 (1H, m), 4.02 (1H, d, J=16 Hz), 5.20 (1H, m), 5.80 (1H, br s)

EXAMPLE 10

To a mixture of 6-hydroxy-5-methoxy-4-[2-methyl-3-(3-methyl-2-butenyl)oxiranyl]-1-oxaspiro[2,5]octane (423 mg) and pyridine (474 mg) in dichloromethane (9 ml) was added portionwise 4-nitrophenyl chloroformate (1.2 g) at ambient temperature. After stirring for 3 hours, 5-methoxy-4-[2-methyl-3-(3-methyl-2-butenyl)oxiranyl]-6-(4-nitrophenoxycarbonyloxy)-1-oxaspiro[2,5]octane was prepared in the reaction mixture. To the mixture 3-amino-1-propanol (2.25 g) was added in one portion. The mixture was stirred for 2 hours at ambient temperature and then diluted with diethyl ether (20 ml). The solution was washed with brine, 1N aqueous hydrochloric acid, 1N aqueous sodium hydroxide, and brine successively. The solvent was dried and evaporated in vacuo to give a crude oil, which was purified by column chromatography on silica gel eluted by ethyl acetate to yield 6-(3-hydroxypropylcarbamoyloxy)-5-methoxy-4-[2-methyl-3-(3-methyl-2-butenyl)oxiranyl]-1-oxaspiro[2,5]octane (400 mg) as crystals.

mp: 56°–58° C.

IR (Nujol): 3350, 1680, 1530, 1260 cm$^{-1}$

NMR (CDCl$_3$, δ): 1.00–1.13 (1H, m), 1.21 (3H, s), 1.65 (3H, s), 1.73 (3H, s), 1.65–2.50 (10H, m), 2.52–2.61 (2H, m), 2.98 (1H, d, J=4 Hz), 3.20–3.45 (1H, m), 3.48 (3H, s), 3.58–3.75 (4H, m), 5.20 (1H, br t, J=8 Hz), 5.50 (1H, br s)

EXAMPLE 11

To a mixture of 6-(3-hydroxypropylcarbamoyloxy)-5-methoxy-4-[2-methyl-3-(3-methyl-2-butenyl)oxiranyl]-1-oxaspiro[2,5]octane (15 mg) and pyridine (12.3 mg) in dichloromethane (1 ml) was added portionwise 4-nitrophenyl chloroformate (32 mg) at ambient temperature. After stirring for 2 hours, 5-methoxy-4-[2-methyl-3-(3-methyl-2-butenyl)oxiranyl]-6-(4-nitrophenoxycarbonyloxypropylcarbamoyloxy)-1-oxaspiro[2,5]octane was prepared in the reaction mixture. To the mixture, 30% methanol solution of methylamine (7 mg) was added in one portion. The mixture was stirred for 1 hour at ambient temperature and diluted with diethyl ether (5 ml). The solution was washed with brine, 1N aqueous hydrochloric acid, 1N aqueous sodium hydroxide, and brine successively. The solvent was dried and evaporated in vacuo to give a crude oil, which was purified by column chromatography on silica gel eluted by diethyl ether to yield 5-methoxy-4-[2-methyl-3-[3-methyl-2-butenyl)oxiranyl]-6-[3-(methylcarbamoyloxy)propylcarbamoyloxy]-1-oxaspiro [2,5]octane (13.8 mg) as crystals.

mp: 52°–54° C.

IR (Nujol): 3350, 1700, 1525, 1460, 1110 cm$^{-1}$

NMR (CDCl$_3$, δ): 1.00–1.12 (1H, m), 1.71 (3H, s), 1.78 (3H, s), 1.80 (3H, s), 1.81–2.48 (9H, m), 2.50–2.62 (2H, m), 2.97 (3H, d, J=4 Hz), 2.98 (1H, d, J=4 Hz), 3.10–3.38 (2H, m), 3.45 (3H, s), 3.64 (1H, dd, J=3 Hz and 11 Hz), 4.02–4.38 (2H, m), 4.93–5.13 (1H, m), 5.13–5.25 (1H, m), 5.50 (1H, br s)

EXAMPLE 12

To a mixture of 6-hydroxy-5-methoxy-4-[2-methyl-3-(3-methyl-2-butenyl)oxiranyl]-1-oxaspiro[2,5]octane (9.2 g) and pyridine (10.3 g) in dichloromethane (92 ml) was added portionwise 4-nitrophenyl chloroformate (13.1 g) at ambient temperature. After stirring for 3 hours, 5-methoxy-4-[2-methyl-3-(3-methyl-2-butenyl)oxiranyl]-6-(4-nitrophenoxycarbonyloxy)-1-oxaspiro[2,5]octane was prepared in the reaction mixture. To the mixture morpholine (28.4 g) was added in one portion. The solution was stirred for 8 hours at ambient temperature and then diluted with diethyl ether (300 ml). The solution was washed with brine, 1N aqueous hydrochloric acid, 1N aqueous sodium hydroxide and brine successively. The solvent was dried and evaporated in vacuo to give 5-methoxy-4-[2-methyl-3-(3-methyl-2-butenyl)oxiranyl]-6-morpholinocarbonyloxy-1-oxaspiro[2,5]octane (13.1 g) as an oil.

IR (CHCl$_3$) 1690, 1430, 1205 cm$^{-1}$

NMR (CDCl$_3$, δ) 1.05–1.17 (1H, m), 1.20 (3H, s), 1.57 (3h, s), 1.73 (3H, s), 1.79–2.46 (6H, m), 2.54 (1H, d, J=4 Hz), 2.60 (1H, t, J=6 Hz), 3.00 (1H, d, J=4 Hz), 3.47 (3H, s), 3.36–3.58 and 3.58–3.75 (9H, m), 5.22 (1H, m), 5.58 (1H, m)

EXAMPLE 13

The following compounds were prepared in a similar manner to that of Example 12.

(1) 5-Methoxy-4-[2-methyl-3-(3-phenyl-2-propenyl) oxiranyl]-6-methylcarbamoyloxy-1-oxaspiro[2,5]octane mp: 45° C.

IR (CHCl$_3$): 3450, 1705 cm$^{-1}$

NMR (CDCl$_3$, δ) 0.98–1.13 (1H, m), 1.26 (3H, s), 1.78–2.15 (4H, m), 2.43–2.64 (2H, m), 2.56 (1H, d, J=4 Hz), 2.72 (1H, t, J=6 Hz), 2.78 (3H, d, J=5 Hz), 2.95 (1H, d, J=4 Hz), 3.47 (3H, s), 3.66 (1H, dd, J=12 and 3 Hz), 4.66–4.83 (1H, br s), 5.46–5.56 (1H, br s), 6.24 (1H, dt, J=16 and 7 Hz), 6.56 (1H, d, J=16 Hz), 7.19–7.41 (5H, m)

(2) 5-Methoxy-4-[2-methyl-3-(3-methyl-2-butenyl) oxiranyl]-6-(3-methylthiopropylcarbamoyloxy)-1-oxaspiro [2,5]octane Oil IR (CHCl$_3$): 3450, 1705 cm$^{-1}$ NMR (CDCl$_3$, δ) 1.00–1.16 (1H, m), 1.23 (3H, s), 1.68 (3H, s), 1.76 (3H, s), 1.72–2.48 (8H, m), 2.13 (3H, s), 2.48–2.65 (4H, m), 3.00 (1H, d, J=4 Hz), 3.30 (2H, dt, J=7 Hz), 3.47 (3H, s), 3.66 (1H, dd, J=12 and 2 Hz), 4.81–4.97 (1H, m), 5.22 (1H, br t, J=7 Hz), 5.44–5.56 (1H, br s)

(3) 6-(4-Ethoxycarbonylpiperazinocarbonyloxy)-5-methyl-4-[2-methyl-3-(3-methyl-2-butenyl)oxiranyl]-1-oxaspiro[2,5]octane mp 88°–89° C.

IR (Nujol) 1690, 1230 cm$^{-1}$

NMR (CDCl$_3$, δ): 1.05–1.18 (1H, m), 1.22 (3H, s), 1.28 (3H, t, J=7 Hz), 1.66 (3H, s), 1.75 (3H, s), 1.78–2.13 (4H, m), 2.20 (1H, br t, J=7 Hz), 2.26–2.48 (1H, m), 2.56 (1H, d, J=4 Hz), 2.57 (1H, t, J=6 Hz), 3.00 (1H, d, J=4 Hz), 3.47 (3H, s), 3.38–3.60 (8H, br s), 3.65 (1H, dd, J=2 Hz and 12 Hz), 4.16 (2H, q, J=7 Hz), 5.20 (1H, br t, J=7 Hz), 5.58 (1H, br s)

(4) 6-(N-Hydroxyethyl-N-methylcarbamoyloxy)-5-methoxy-4-[2-methyl-3-(3-methyl-2-butenyl)oxiranyl]-1-oxaspiro[2,5]octane Oil IR (CHCl$_3$) 3450, 1680 cm$^{-1}$ NMR (CDCl$_3$) 1.02–1.16 (1H, m), 1.21 (3H, s), 1.65 (3H, s), 1.75 (3H, s), 1.80–2.25 (5H, m), 2.27–2.48 (1H, m), 2.55 (1H, d, J=4 Hz), 2.58 (1H, t, J=5 Hz), 2.66–2.95 (1H, br), 2.96 (3H, s), 2.98 (1H, d, J=4 Hz), 3.45 (3H, s), 3.40–3.48 (2H, br s), 3.64 (1H, dd, J=12, 2 Hz), 3.69–3.83 (2H, m), 5.20 (1H, br t, J=7 Hz), 5.46–5.62 (1H, br s)

EXAMPLE 14

To a mixture of 6-hydroxy-5-methoxy-4-[2-methyl-3-(3-methyl-2-butenyl)oxiranyl]-1-oxaspiro[2,5]octane (26 mg), pyridine (44 µl), and 4-dimethylaminopyridine (2 mg) in dichloromethane (0.8 ml) was added dropwise 4-nitrophenyl chloroformate (20 mg) at ambient temperature. After stirring for 2 hours, piperidine (40 µl) was added in one portion. The solution was stirred overnight at ambient temperature and then diluted with diethyl ether (20 ml). The mixture was washed with brine, aqueous saturated sodium bicarbonate solution, and brine successively. The mixture was dried and evaporated under reduced pressure to give a crude oil, which was purified by preparative thin layer chromatography to yield 5-methoxy-4-[2-methyl-3-(3-methyl-2-butenyl) oxiranyl]-6-piperidinocarbonyloxy-1-oxaspiro[2,5]octane (34.3 mg).

Oil

IR (CHCl$_3$): 1680 cm$^{-1}$

NMR (CDCl$_3$, δ) 1.03–1.16 (1H, m), 1.22 (3H, s), 1.66 (3H, s), 1.74 (3H, s), 1.46–2.46 (12H, m), 2.52 (1H, d, J=4 Hz), 2.58 (1H, t, J=6 Hz), 2.99 (1H, d, J=4 Hz), 3.33–3.53 (4H, m), 3.46 (3H, s), 3.64 (1H, dd, J=2 Hz and 12 Hz), 5.21 (1H, br t, J=8 Hz), 5.55 (1H, br s)

EXAMPLE 15

The following compounds were prepared in a similar manner to that of Example 14.

(1) 5-Methoxy-4-[2-methyl-3-(3-methyl-2-butenyl) oxiranyl-6-(4-methylpiperidinocarbonyloxy)-1-oxaspiro[2, 5]octane Oil IR (CHCl$_3$): 1680 cm$^{-1}$ NMR (CDCl$_3$): 0.94 (3H, d, J=7 Hz), 1.00–1.36 (3H, m), 1.22 (3H, s), 1.67 (3H, s), 1.75 (3H, s), 1.40–2.48 (9H, m), 2.54 (1H, d, J=4 Hz), 2.58 (1H, t, J=7 Hz), 2.63–2.92 (2H, m), 3.00 (1H, d, J=4 Hz), 3.45 (3H, s), 3.64 (1H, dd, J=2 Hz and 12 Hz), 3.87–4.30 (2H, m), 5.20 (1H, t, J=7 Hz), 5.55 (1H, br s)

(2) 5-Methoxy-4-[2-methyl-3-(3-methyl-2-butenyl) oxiranyl]-6-thiomorpholinocarbonyloxy-1-oxaspiro[2,5] octane mp: 71°–72° C.

IR (Nujol): 1690, 1200, 1110 cm$^{-1}$

NMR (CDCl$_3$, δ): 1.04–1.17 (1H, m), 1.21 (3H, s), 1.66 (3H, s), 1.74 (3H, s), 1.78–2.27 (5H, m), 2.28–2.46 (1H, m), 2.46–2.75 (6H, m), 3.00 (1H, d, J=4 Hz), 3.45 (3H, s), 3.65 (1H, dd, J=2 Hz and 12 Hz), 3.63–3.83 (4H, m), 5.21 (1H, br t, J=7 Hz), 5.56 (1H, br s)

(3) 5-Methoxy-4-[2-methyl-3-(3-methyl-2-butenyl)oxiranyl]-6-piperidinocarbamoyloxy-1-oxaspiro[2.5]octane Oil IR (CHCl₃) 3450, 1680 cm⁻¹

NMR (CDCl₃, δ): 1.03–1.16 (1H, m), 1.22 (3H, s), 1.66 (3H, s), 1.75 (3H, s), 1.80–2.48 (6H, m), 1.43–1.70 (6H, m), 2.54 (1H, d, J=4 Hz), 2.58 (1H, t, J=6 Hz), 3.00 (1H, d, J=4 Hz), 3.30–3.53 (4H, m), 3.46 (3H, s), 3.65 (1H, dd, J=2 Hz and 12 Hz), 5.21 (1H, br t, J=7 Hz), 5.55 (1H, br s)

(4) 5-Methoxy-4-[2-methyl-3-(3-methyl-2-butenyl)oxiranyl]-6-[3-(2-oxopyrrolidin-1-yl)propylcarbamoyloxy]-1-oxaspiro[2.5]octane Oil IR (CHCl₃) 3450, 1700, 1660 cm⁻¹

NMR (CDCl₃, δ): 0.97–1.14 (1H, m), 1.21 (3H, s), 1.66 (3H, s), 1.75 (3H, s), 1.63–2.26 (9H, m), 2.27–2.49 (3H, m), 2.52 (1H, d, J=4 Hz), 2.57 (1H, t, J=5 Hz), 2.98 (1H, d, J=4 Hz), 3.06–3.26 (2H, m), 3.30–3.52 (4H, m), 3.47 (3H, s), 3.63 (1H, dd, J=2 Hz and 12 Hz), 5.21 (1H, br t, J=7 Hz), 5.46–5.65 (2H, m)

(5) 5-Methoxy-4-[2-methyl-3-(3-methyl-2-butenyl)oxiranyl]-6-morpholinocarbonyloxy-1-oxaspiro[2.5]octane mp: 122°–123° C.

IR (Nujol): 3250, 1700, 1525, 1250, 1150, 1100 cm⁻¹

NMR (CDCl₃, δ): 1.04–1.16 (1H, m), 1.22 (3H, s), 1.65 (3H, s), 1.75 (3H, s), 1.78–2.48 (6H, m), 2.55 (1H, d, J=4 Hz), 2.56 (1H, t, J=6 Hz), 2.76–2.93 (4H, br t, J=5 Hz), 3.64 (1H, dd, J=12 and 2 Hz), 3.45 (3H, s), 3.73–3.86 (4H, br t, J=5 Hz), 5.20 (1H, br t, J=7 Hz), 5.52 (1H, br s), 5.74 (1H, br s)

(6) 5-Methoxy-6-(2-methoxyethylcarbamoyloxy)-4-[2-methyl-3-(3-methyl-2-butenyl)oxiranyl]-1-oxaspiro[2.5]octane Oil IR (CHCl₃) 1700, 1510, 1440, 1380, 1200 cm⁻¹

NMR (CDCl₃, δ): 0.96–1.12 (1H, m), 1.22 (3H, s), 1.68 (3H, s), 1.75 (3H, s), 1.77–2.48 (6H, m), 2.55 (1H, d, J=4 Hz), 2.57 (1H, t, J=8 Hz), 2.98 (1H, d, J=4 Hz), 3.28–3.41 (2H, m), 3.38 (3H, s), 3.41–3.52 (2H, m), 3.45 (3H, s), 3.64 (1H, dd, J=3 Hz and 12 Hz), 5.05–5.28 (2H, m), 5.50 (1H, br s)

(7) 6-(4-Hydroxypiperidinocarbonyloxy)-5-methoxy-4-[2-methyl-3-(3-methyl-2-butenyl)oxiranyl]-1-oxaspiro[2.5]octane Oil IR (CHCl₃): 3530, 1720, 1110 cm⁻¹

NMR (CDCl₃): 1.02–1.16 (1H, m), 1.22 (3H, s), 1.66 (3H, s), 1.75 (3H, s), 1.40–2.47 (11H, m), 2.55 (1H, d, J=4 Hz), 2.57 (1H, t, J=6 Hz), 3.00 (1H, d, J=4 Hz), 3.02–3.22 (2H, m), 3.45 (3H, s), 3.64 (1H, dd, J=2 Hz and 12 Hz), 3.74–3.99 (3H, m), 5.20 (1H, br t, J=7 Hz), 5.56 (1H, br s)

(8) 6-(2-Hydroxymethylpyrrolidinocarbonyloxy)-5-methoxy-4-[2-methyl-3-(3-methyl-2-butenyl)oxiranyl]-1-oxaspiro[2.5]octane Oil IR (Neat): 3450, 1680, 1420, 1105 cm⁻¹

NMR (CDCl₃, δ): 1.04–1.16 (1H, m), 1.20 (3H, s), 1.66 (3H, s), 1.75 (3H, s), 1.75–2.48 (1H, m), 2.55 (1H, d, J=4 Hz), 2.57 (1H, t, J=6 Hz), 2.98 (1H, d, J=4 Hz), 3.35–3.80 (8H, m), 3.90–4.04 (1H, m), 5.20 (1H, br t, J=8 Hz), 5.60 (1H, br s)

(9) 5-Methoxy-6-(2-methoxymethylpyrrolidinocarbonyloxy)-4-[2-methyl-3-(3-methyl-2-butenyl)oxiranyl]-1-oxaspiro[2.5]octane Oil IR (Neat) 1690, 1410, 1100 cm⁻¹

NMR (CDCl₃, δ): 1.00–1.18 (1H, m), 1.20 (3H, s), 1.65 (3H, s), 1.75 (3H, s), 1.77–2.46 (11H, m), 2.50–2.60 (2H, m), 2.98 (1H, d, J=4 Hz), 3.15–3.58 (10H, m), 3.90–4.08 (1H, m), 5.20 (1H, br t, J=8 Hz), 5.60 (1H, br s)

(10) 5-Methoxy-4-[2-methyl-3-(3-methyl-2-butenyl)oxiranyl]-6-(3-methylthiopropylcarbamoyloxy)-1-oxaspiro[2.5]octane Oil IR (CHCl₃): 3450, 1705 cm⁻¹

NMR (CDCl₃, δ) 1.00–1.16 (1H, m), 1.23 (3H, s), 1.68 (3H, s), 1.76 (3H, s), 1.72–2.48 (8H, m), 2.13 (3H, s), 2.48–2.65 (4H, m), 3.00 (1H, 4 Hz), 3.30 (2H, td, J=7 Hz and 7 Hz), 3.47 (3H, s), 3.66 (1H, dd, J=2 Hz and 12 Hz), 4.81–4.97 (1H, m), 5.22 (1H, br t, J=7 Hz), 5.44–5.56 (1H, br s)

(11) 6-(2-Hydroxyethylcarbamoyloxy)-5-methoxy-4-[2-methyl-3-(3-methyl-2-butenyl)oxiranyl]-1-oxaspiro[2.5]octane mp: 57°–58° C.

IR (Neat): 3355, 1710, 1525, 1250, 1100 cm⁻¹

NMR (CDCl₃, δ): 1.06 (1H, m), 1.22 (3H, s), 1.67 (3H, s), 1.83 (3H, s), 1.85–2.48 (6H, m), 2.50–2.62 (2H, m), 2.72 (1H, br t, J=5 Hz), 2.98 (1H, d, J=4 Hz), 3.20–3.51 (2H, m), 3.46 (3H, s), 3.59–3.78 (3H, m), 5.11–5.35 (2H, m), 5.52 (1H, br s)

(12) 5-Methoxy-6-(3-methoxypropylcarbamoyloxy)-4-[2-methyl-3-(3-methyl-2-butenyl)oxiranyl]-1-oxaspiro-[2.5]octane mp: 55°–56° C.

IR (CHCl₃, δ) 3460, 1710, 1105 cm⁻¹

NMR (CDCl₃, δ): 0.96–1.14 (1H, m), 1.21 (3H, s), 1.66 (3H, s), 1.74 (3H, s), 1.68–2.46 (8H, m), 2.54 (1H, d, J=6 Hz), 2.56 (1H, t, J=7 Hz), 2.97 (1H, d, J=6 Hz), 3.19–3.37 (2H, m), 3.33 (3H, s), 3.44 (3H, s), 3.38–3.50 (2H, m), 3.64 (1H, dd, J=14, 2 Hz), 4.96–5.10 (1H, m), 5.21 (1H, br t, J=7 Hz), 5.44–5.52 (1H, br s)

(13) 6-[(3-Ethoxycarbonyl)propylcarbamoyloxy]-5-methoxy-4-[2-methyl-3-(3-methyl-2-butenyl)oxiranyl]-1-oxaspiro[2.5]octane Oil IR (CHCl₃): 3440, 1715, 1505 cm⁻¹

NMR (CDCl₃): 0.9.9–1.14 (1H, m), 1.21 (3H, s), 1.26 (3H, t, J=7 Hz), 1.65 (3H, s), 1.74 (3H, s), 1.76–2.26 (6H, m), 2.27–2.48 (4H, m), 2.55 (1H, d, J=6 Hz), 2.52–2.60 (1H, m), 2.97 (1H, d, J=6 Hz), 3.12–3.32 (2H, m), 3.45 (3H, s), 3.64 (1H, dd, J=14, 2 Hz), 4.14 (2H, q, J=7 Hz), 4.89 (1H, br s), 5.12–5.26 (1H, m), 5.50 (1H, br s)

EXAMPLE 16

The following compounds were prepared in a similar manner to that of Example 11.

(1) 5-Methoxy-6-(4-methylcarbamoyloxypiperidinocarbonyloxy)-4-[2-methyl-3-(3-methyl-2-butenyl)oxiranyl]-1-oxaspiro[2.5]octane mp: 44°–47° C.

IR (Nujol): 3350, 1720, 1690 cm⁻¹

NMR (CDCl₃, δ): 1.02–1.16 (1H, m), 1.21 (3H, s), 1.65 (3H, s), 1.75 (3H, s), 1.47–2.25 (9H, m), 2.36–2.48 (1H, m), 2.55 (1H, d, J=4 Hz), 2.57 (1H, t, J=6 Hz), 2.81 (3H, d, J=5 Hz), 3.01 (1H, d, J=4 Hz), 3.18–3.40 (2H, m), 3.46 (3H, s), 3.56–3.83 (2H, m), 3.64 (1H, dd, J=2 Hz and 12 Hz), 4.54–4.70 (1H, br s), 4.74–4.95 (1H, br s), 5.20 (1H, br t, J=7 Hz), 5.57 (1H, br s)

(2) 5-Methoxy-4-[2-methyl-3-(3-methyl-2-butenyl)oxiranyl]-6-[N-[2-(thiomorpholin-4-ylcarbonyloxy)ethyl]-N-methylcarbamoyloxy]-1-oxaspiro[2.5]octane Oil IR (CHCl$_3$): 1680, 1460, 1420, 1100 cm$^{-1}$ NMR (CDCl$_3$, δ): 1.02–1.17 (1H, m), 1.21 (3H, s), 1.66 (3H, s), 1.75 (3H, s), 1.60–2.48 (6H, m), 2.50–2.75 (6H, m), 2.87–3.10 (4H, m), 3.46 (3H, s), 3.52–3.86 (7H, m), 4.15–4.34 (2H, m), 5.20 (1H, br t, J=7 Hz), 5.56 (1H, br s)

(3) 6-[3-(N-Hydroxyethyl-N-methylcarbamoyloxy) propylcarbamoyloxy]-5-methoxy-4-[2-methyl-3-(3-methyl-2-butenyl)oxiranyl]-1-oxaspiro[2.5]octane Oil IR (CHCl$_3$): 3450, 1680 cm$^{-1}$ NMR (CDCl$_3$, δ): 0.81–0.96 (2H, m), 0.97–1.13 (1H, m), 1.20 (3H, s), 1.65 (3H, s), 1.73 (3H, s), 1.68–2.25 (7H, m), 2.26–2.48 (1H, m), 2.54 (1H, d, J=4 Hz), 2.56 (1H, t, J=6 Hz), 2.97 (4H, s), 3.16–3.40 (2H, m), 3.43 (3H, s), 3.40–3.52 (2H, m), 3.64 (1H, dd, J=12, 2 Hz), 3.68–3.85 (2H, br s), 4.19 (2H, t, J=6 Hz), 5.20 (1H, br t, J=7 Hz), 5.32–5.55 (1H, m)

(4) 5-Methoxy-4-[2-methyl-3-(3-methyl-2-butenyl) oxiranyl]-6-[3-(morpholinocarbonyloxy) propylcarbamoyloxy]-1-oxaspiro[2.5]octane Oil IR (CHCl$_3$): 3450, 1690 cm$^{-1}$ NMR (CDCl$_3$, δ): 0.98–1.13 (1H, m), 1.20 (3H, s), 1.65 (3H, s), 1.74 (3H, s), 1.72–2.26 (7H, m), 2.27–2.48 (1H, m), 2.54 (1H, d, J=4 Hz), 2.56 (1H, t, J=5 Hz), 2.98 (1H, d, J=4 Hz), 3.15–3.36 (2H, m), 3.44 (3H, s), 3.42–3.52 (4H, m), 3.56–3.72 (5H, m), 4.17 (2H, t, J=7 Hz), 4.98 (1H, br t, J=7 Hz), 5.20 (1H, br t, J=7 Hz), 5.49 (1H, br s)

(5) 5-Methoxy-4-[2-methyl-3-(3-methyl-2-butenyl) oxiranyl]-6-[2-(methylcarbamoyloxy)ethylcarbamoyloxy]-1-oxaspiro[2.5]octane Oil IR (Neat): 3350, 1710, 1530, 1250 cm$^{-1}$ NMR (CDCl$_3$, δ): 0.98–1.15 (1H, m), 1.21 (3H, s), 1.64 (3H, s), 1.75 (3H, s), 1.75–2.45 (6H, m), 2.50–2.61 (2H, m), 2.78 (3H, d, J=5 Hz), 2.96 (1H, d, J=4 Hz), 3.40 (2H, m), 3.45 (3H, s), 3.62 (1H, dd, J=11 and 3 Hz), 4.15 (2H, br t, J=5 Hz), 4.77 (1H, br s), 5.08 (1H, br s), 5.20 (1H, t, J=7 Hz), 5.48 (1H, br s)

(6) 5-Methoxy-4-[2-methyl-3-(3-methyl-2-butenyl) oxiranyl]-6-[4-(methylcarbamoyloxy)butylcarbamoyloxy]-1-oxaspiro[2.5]octane Oil IR (Neat): 3350, 1700, 1530, 1255, 1130, 1100 cm$^{-1}$ NMR (CDCl$_3$, δ): 0.98–1.12 (1H, m), 1.20 (3H, s), 1.65 (3H, s), 1.74 (3H, s), 1.45–2.48 (10H, m), 2.49–2.61 (2H, m), 2.78 (3H, d, J=5 Hz), 2.97 (1H, d, J=4 Hz), 3.10–3.28 (2H, m), 3.45 (3H, s), 3.62 (1H, dd, J=15 and 3 Hz), 4.00–4.13 (2H, m), 4.60–4.84 (2H, m), 5.20 (1H, br d, J=7 Hz), 5.47 (1H, br s)

(7) 5-Methoxy-6-(3-methylcarbamoyloxy-2-propenylcarbonyloxy)-4-[2-methyl-3-(3-methyl-2-butenyl) oxiranyl]-1-oxaspiro[2.5]octane Oil IR (CHCl$_3$): 3460, 1715 cm$^{-1}$ NMR (CDCl$_3$, δ): 1.02–1.16 (1H, m), 1.23 (3H, s), 1.67 (3H, s), 1.75 (3H, s), 1.82–2.48 (6H, m), 2.56 (1H, d, J=4 Hz), 2.60 (1H, t, J=6 Hz), 2.86 (3H, d, J=5 Hz), 3.00 (1H, d, J=4 Hz), 3.44 (3H, s), 3.69 (1H, dd, J=3 Hz and 12 Hz), 4.70–4.90 (3H, m), 5.22 (1H, br t, J=7 Hz), 5.69 (1H, br s), 6.06 (1H, d, J=16 Hz), 6.95 (1H, td, J=4 Hz and 16 Hz)

EXAMPLE 17

To a solution of 6-cyclohexylcarbamoyloxy-5-methoxy-4-[2-methyl-3-(3-methyl-2-butenyl)oxiranyl]-1-oxaspiro[2,5]octane (20 mg) in a mixture of methanol (0.1 ml) and dichloromethane (5 ml) was passed through ozone at –78° C. for 3 minutes. Nitrogen was bubbled into the solution at the same temperature to remove excess ozone. The solvents were evaporated and the residue was dissolved in methanol (2 ml). To the solution was added sodium borohydride (10 mg) in one portion at 5° C. The mixture was stirred at 5° C. for 10 minutes and then concentrated in vacuo. The residue was dissolved in dichloromethane (20 ml), washed with brine, dried, and evaporated. The crude oil was purified by column chromatography on silica gel eluted with diethyl ether to yield 6-cyclohexylcarbamoyloxy-4-[3-(2-hydroxyethyl)-2-methyloxiranyl]-5-methoxy-1-oxaspiro[2, 5]-octane (11.6 mg).

Oil

IR (CHCl$_3$): 3440, 1705, 1050 cm$^{-1}$

NMR (CDCl$_3$, δ) 1.22 (3H, s), 1.00–2.15 (18H, m), 2.59 (1H, d, J=4 Hz), 2.77 (1H, dd, J=5 Hz and 5 Hz), 2.91 (1H, d, J=4 Hz), 3.46 (3H, s), 3.35–3.55 (1H, m), 3.66 (1H, dd, J=2 Hz and 12 Hz), 3.87 (2H, br s), 4.69 (1H, d, J=7 Hz), 5.45 (1H, br s)

EXAMPLE 18

The following compound was prepared in a similar manner to that of Example 17.

4-[3-(2-Hydroxyethyl)-2-methyloxiranyl]-5-methoxy-6-morpholinocarbonyloxy-1-oxaspiro[2,5]octane Oil IR (CHCl$_3$): 3450, 1680, 1420, 1200 cm$^{-1}$ NMR (CDCl$_3$, δ): 1.10–1.22 (1H, m), 1.20 (3H, s), 1.61–2.11 (6H, m), 2.60 (1H, d, J=4 Hz), 2.80 (1H, dd, J=8 and 5 Hz), 2.94 (1H, d, J=4 Hz), 3.48 (3H, s), 3.35–3.55 (5H, m), 3.55–3.76 (5H, m), 3.76–3.95 (2H, m), 5.55 (1H, br s)

EXAMPLE 19

To a solution of 6-cyclohexylcarbamoyloxy-5-methoxy-4-[2-methyl-3-(3-methyl-2-butenyl)oxiranyl]-1-oxaspiro[2, 5]octane (70 mg) in a mixture of methanol (0.1 ml) and dichloromethane (5 ml) was passed through ozone for 13 minutes at –78° C. to give 6-cyclohexylcarbamoyloxy-5-methoxy-4-[2-methyl-3-formylmethyloxiranyl]-1-oxaspiro [2,5]octane in the reacting mixture. After babbling of nitrogen, methyl sulfide (0.2 ml) was added to the mixture at the same temperature. The mixture was stirred at –78° C. for 15 minutes and allowed to warm to 0° C. followed by the addition of carboethoxymethylene-triphenylphosphorane (150 mg). The mixture was stirred at ambient temperature for 18 hours and concentrated in vacuo. The residue was purified by column chromatography on silica gel eluted with a mixture of diethyl ether and n-hexane (1:1) to yield 6-cyclohexylcarbamoyloxy-4-[3-(3-ethoxycarbonyl-2-propenyl)-2-methyloxiranyl]-5-methoxy-1-oxaspiro[2,5]-octane (53 mg) as an oil.

IR (CHCl$_3$) 3450, 1705 cm$^{-1}$

NMR (CDCl$_3$, δ): 1.01–1.17 (1H, m), 1.22 (3H, s), 1.28 (3H, t, J=7 Hz), 1.19–2.14 (15H, m), 2.40–2.50 (2H, m), 2.58 (1H, d, J=4 Hz), 2.71 (1H, dd, J=5 Hz and 7 Hz), 2.82 (1H, d, J=4 Hz), 3.45 (3H, s), 3.42–3.52 (1H, m), 3.65 (1H, dd, J=2 Hz and 12 Hz), 4.20 (2H, q, J=7 Hz), 4.66 (1H, br d, J=7 Hz), 6.01 (1H, d, J=15 Hz), 7.00 (1H, dt, J=6 Hz and 15 Hz)

EXAMPLE 20

To a solution of 6-(4,5-dihydroxy-2-hexenoyloxy)-5-methoxy-4-(2-methyl-3-(3-methyl-2-butenyl)oxiranyl]-1- oxaspiro[2,5]octane (412 mg) in a mixture of methanol (4 ml) and water (4 ml) was added sodium periodate (215 mg) in several portions at 5° C. The mixture was stirred for half hour at the same temperature and diluted with diethyl ether (30 ml). The mixture was washed with brine, dried, and concentrated in vacuo to give a crude oil, which was purified by column chromatography on silica gel (elution by diethyl ether/n-hexane=1/1) to yield 6-(3-formylacryloyloxy)-5-methoxy-4-(2-methyl-3-(3-methyl-2-butenyl)oxiranyl]-1-oxaspiro[2,5]octane (251 mg) as an oil.

IR (CHCl$_3$) 1720, 1695 cm$^{-1}$

NMR (CDCl$_3$, δ): 1.06–1.20 (1H, m), 1.22 (3H, s), 1.66 (3H, s), 1.75 (3H, s), 1.89–2.48 (6H, m), 2.58 (1H, d, J=4 Hz), 2.60 (1H, t, J=5 Hz), 3.02 (1H, d, J=4 Hz), 3.46 (3H, s), 3.72 (1H, dd, J=2 Hz and 12 Hz), 5.22 (1H, br t, J=7 Hz), 5.70 (1H, br s), 6.78 (1H, d, J=16 Hz), 6.98 (1H, dd, J=6 Hz and 16 Hz), 9.78 (1H, d, J=6 Hz)

EXAMPLE 21

To a solution of 5-methoxy-4-[2-methyl-3-(3-methyl-2-butenyl)oxiranyl]-6-(thiomorpholin-4-ylcarbonyloxy)-1-oxaspiro[2,5]octane (41 mg) in 1,4-dioxane (2 ml) and water (0.2 ml) was added sodium periodate (21 mg) at ambient temperature. After stirring at the same temperature for 18 hours, the reaction mixture was diluted with diethyl ether. The precipitates were filtered off by celite and the filtrate was concentrated in vacuo. The residue was purified by column chromatography on silica gel (elution by ethyl acetate) to yield 5-methoxy-4-[2-methyl-3-(3-methyl-2-butenyl)oxiranyl]-6-(1-oxothiomorpholin-4-ylcarbonyloxy)-1-oxaspiro[2,5]octane (25 mg) as an oil.

IR (CHCl$_3$): 1690, 1100, 900 cm$^{-1}$

NMR (CDCl$_3$, δ): 1.08–1.20 (1H, m), 1.21 (3H, s), 1.68 (3H, s), 1.77 (3H, s), 1.72–2.29 (5H, m), 2.30–2.50 (1H, m), 2.60 (1H, d, J=4 Hz), 3.02 (1H, d, J=4 Hz), 2.50–3.06 (5H, m), 3.47 (3H, s), 3.66 (1H, dd, J=12, 2 Hz), 3.82–4.18 (4H, m), 5.21 (1H, br t, J=7 Hz), 5.65 (1H, br s).

EXAMPLE 22

To a solution of 5-methoxy-4-[2-methyl-3-(3-methyl-2-butenyl)oxiranyl]-6-(thiomorphol in-4-ylcarbonyloxy)-1-oxaspiro[2,5]octane (31 mg) in dichloromethane (2 ml) was added m-chloroperbenzoic acid (31 mg) at 0° C. After stirring at 0° C. for 1 hour, the mixture was diluted with diethyl ether and washed with saturated sodium hydrogen carbonate and brine. The mixture was dried and concentrated to give a crude oil which was purified by preparative thin layer chromatography to yield 5-methoxy-4-[2-methyl-3-(3-methyl-2-butenyl)oxiranyl]-6-(1,1-dioxothiomorpholin-4-ylcarbonyloxy)-1-oxaspiro[2,5]octane (9 mg) as an oil.

IR (CHCl$_3$) 1700, 1130 cm$^{-1}$

NMR (CDCl$_3$, δ): 0.75–0.98 (1H, m), 1.20 (3H, s), 1.66 (3H, s), 1.75 (3H, s), 2.47–2.60 (1H, m), 2.56 (1H, d, J=4 Hz), 3.00 (1H, d, J=4 Hz), 1.06–2.45 (6H, m), 2.84–3.13 (4H, br s), 3.45 (3H, s), 3.65 (1H, dd, J=12, 2 Hz), 3.72–4.26 (4H, br s), 5.20 (1H, br t, J=7 Hz), 5.59 (1H, br s)

EXAMPLE 23

To a solution of 6-(4,5-dihydroxy-2-hexanoyloxy)-5-methoxy-4-[2-methyl-3-(3-methyl-2-butenyl)oxiranyl]-1-oxaspiro[2,5]octane (99 mg) in a mixture of methanol (2 ml) and water (2 ml) was added sodium periodate (62 mg) in one portion at 5° C. After stirring for half an hour at the same temperature, the mixture was treated with sodium borohydride (46 mg) for half an hour. The mixture was poured into ice water and the separated oil was extracted with diethyl ether. The organic layer was dried and concentrated in vacuo to give 6-(4-hydroxycrotonoyloxy)-5-methoxy-4-[2-methyl-3-(3-methyl-2-butenyl)oxiranyl]-1-oxaspiro[2,5]-octane (71 mg) as an oil.

IR (CHCl$_3$): 3400, 1705 cm$^{-1}$

NMR (CDCl$_3$, δ): 1.02–1.16 (1H, m), 1.22 (3H, s), 1.67 (3H, s), 1.74 (3H, s), 1.83–2.48 (6H, m), 2.56 (1H, d, J=4 Hz), 2.60 (1H, t, J=6 Hz), 3.00 (1H, d, J=4 Hz), 3.44 (3H, s), 3.68 (1H, dd, J=2 Hz and 12 Hz), 4.31–4.48 (2H, m), 5.21 (1H, br t, J=7 Hz), 5.71 (1H, br s), 6.15 (1H, d, J=16 Hz), 7.04 (1H, td, J=5 Hz and 16 Hz)

EXAMPLE 24

A solution of 5-methoxy-4-[2-methyl-3-(3-methyl-2-butenyl)oxiranyl]-6-morpholinocarbonyloxy-1-oxaspiro[2,5]octane (1.23 g) in ethyl acetate (12 ml) was hydrogenated under hydrogen (1 atm) in the presence of platinum oxide (120 mg) for 1 hour. The catalyst was removed by filtration and the filtrate was concentrated in vacuo. The residue was purified by column chromatography on silica gel eluted with a mixture of diethyl ether and n-hexane (1:1, V/V) to give 5-methoxy-4-[2-methyl-3-(3-methylbutyl)oxiranyl]-6-morpholinocarbonyloxy-1-oxaspiro[2,5]octane (996 mg) as an oil, which was standing on to give crystals.

mp: 64°–65° C.

IR (Nujol) 1700, 1240, 1115 cm$^{-1}$

NMR (CDCl$_3$, δ) 0.90 (6H, d, J=6 Hz), 1.18 (3H, s), 1.08–1.70 (6H, m), 1.80–2.12 (4H, m), 2.55 (1H, dd, J=7 and 5 Hz), 2.60 (1H, d, J=4 Hz), 2.88 (1H, d, J=4 Hz), 3.36–3.55 (8H, m), 3.60–3.77 (4H, m), 5.58 (1H, m)

EXAMPLE 25

The following compounds were prepared in a similar manner to that of Example 24.

(1) 6-Cyclohexylcarbamoyloxy-5-methoxy-4-[2-methyl-3-(3-methylbutyl)oxiranyl]-1-oxaspiro[2,5]octane IR (CHCl$_3$) 3440, 1700 cm$^{-1}$ NMR (CDCl$_3$, δ) 0.91 (6H, d, J=7 Hz), 1.00–2.17 (20H, m), 1.19 (3H, s), 2.53 (1H, dd, J=4 Hz and 7 Hz), 2.58 (1H, d, J=4 Hz), 2.88 (1H, d, J=4 Hz), 3.44 (3H, s), 3.46–3.57 (1H, m), 3.64 (1H, dd, J=2 Hz and 12 Hz), 4.67 (1H, br d, J=7 Hz), 5.45 (1H, br s)

(2) 6-Carbamoyloxy-5-methoxy-4-[2-methyl-3-(3-methylbutyl)oxiranyl]-1-oxaspiro[2,5]octane mp: 93°–94° C.

IR (Nujol) 3450, 3350, 3300, 3200, 1720, 1605, 1320, 1120, 1080 cm$^{-1}$

NMR (CDCl$_3$, δ): 0.90 (6H, d, J=6 Hz), 1.05–2.20 (10H, m), 1.20 (3H, s), 2.55 (1H, dd, J=7 and 5 Hz), 2.62 (1H, d, J=4 Hz), 2.90 (1H, d, J=4 Hz), 3.45 (3H, s), 3.67 (1H, dd, J=11 and 3 Hz), 4.69 (2H, br s), 5.47 (1H, m)

EXAMPLE 26

A solution of 6-cyclohexylcarbamoyloxy-4-[3-(3-ethoxycarbonyl-2-propenyl)-2-methyloxiranyl]-5-methoxy-1-oxaspiro[2,5]octane (46 mg) in ethyl acetate (30 ml) was hydrogenated under hydrogen (1 atm) in the presence of platinum oxide (5 mg) for 2 hours. The catalyst was removed by filtration and the filtrate was concentrated in vacuo. The residue was purified by column chromatography on silica gel eluted with a mixture of diethyl ether and n-hexane (1:1) to give 6-cyclohexylcarbamoyloxy-4-[3-(3-ethoxycarbonylpropyl)-2-methyloxiranyl]-5-methoxy-1-oxaspiro[2,5]octane as an oil.

IR (CHCl₃) 3440, 1710, 900 cm⁻¹

NMR (CDCl₃, δ) 1.18 (3H, s), 1.26 (3H, t, J=6 Hz), 1.00–1.52 (10H, m), 1.52–2.18 (9H, m), 2.28–2.52 (2H, m), 2.59 (1H, dd, J=2 Hz and 5 Hz), 2.60 (1H, d, J=4 Hz), 2.84 (1H, d, J=4 Hz), 3.45 (3H, s), 3.34–3.53 (1H, m), 3.63 (1H, dd, J=3 Hz and 11 Hz), 4.13 (2H, q, J=6 Hz), 4.67 (1H, br d, J=8 Hz), 5.46 (1H, br s)

EXAMPLE 27

To a solution of 4-[3-(2-hydroxyethyl)-2-methyloxiranyl]-5-methoxy-6-(morpholinocarbonyloxy)-1-oxaspiro[2,5]octane (14.4 mg) in a mixture of anhydrous tetrahydrofuran (1 ml) and N,N-dimethylformamide (1 ml) was added sodium hydride (60% oil dispersion, 4.7 mg) in one portion under ice cooling. The mixture was stirred for half an hour at the same temperature and benzylbromide (13.3 mg) was added. After stirred for 2 hours at ambient temperature, the reaction was quenched with water (2 ml) and extracted with diethyl ether (1 ml) three times. The combined organic layers were washed with water, dried, and evaporated in vacuo. The residue was purified by column chromatography on silica gel (diethyl ether/n-hexane=1/1) to give 4-[3-(2-benzyloxyethyl)-2-methyloxiranyl]-5-methoxy-6-(morpholinocarbonyloxy)-1-oxaspiro[2,5]octane (4.8 mg).

mp: 96°–97° C.

IR (CHCl₃): 1690, 1430, 1240, 1105 cm⁻¹

NMR (CDCl₃, δ): 1.02–1.16 (1H, m), 1.19 (3H, s), 1.16–2.10 (6H, m), 2.50 (1H, d, J=4 Hz), 2.78 (1H, dd, J=8 and 5 Hz), 2.94 (1H, d, J=4 Hz), 3.41–3.52 (7H, m), 3.60–3.72 (7H, m), 4.53 (2H, s), 5.55 (1H, m), 7.36 (5H, br s)

EXAMPLE 28

The following compounds were prepared in a similar manner to that of Example 27.

(1) 4-{3-[2-(3,4-Dimethylbenzyloxy)ethyl]-2-methyloxiranyl}-5-methoxy-6-(morpholinocarbonyloxy)-1-oxaspiro[2,5]octane Oil IR (Neat): 1695, 1420, 1240, 1105 cm⁻¹

NMR (CDCl₃, δ): 1.02–1.15 (1H, m), 1.20 (3H, s), 1.61–2.10 (6H, m), 2.22 and 2.28 (each 3H, 2 isomers'), 2.48 and 2.50 (1H, d, J=4 Hz, 2 isomers'), 2.76 (1H, dd, J=8 and 5 Hz), 2.95 and 2.98 (1H, d, J=4 Hz, 2 isomers'), 3.40–3.55 (5H, m), 3.47 (3H, s), 3.55–3.80 (6H, m), 4.48 and 4.55 (2H, 2 isomers'), 5.58 (1H, br s), 7.01–7.20 (3H, m)

(2) 4-{3-[2-(4-chlorobenzyloxy)ethyl]-2-methyloxiranyl}-5-methoxy-6-(morpholinocarbonyloxy)-1-oxaspiro[2,5]octane Oil IR (Neat): 1690, 1420, 1240, 1105 cm⁻¹

NMR (CDCl₃, δ): 1.05–1.16 (1H, m), 1.20 (3H, s), 1.65–2.10 (6H, m), 2.51 (1H, d, J=4 Hz), 2.75 (1H, dd, J=8 and 5 Hz), 2.94 (1H, d, J=4 Hz), 3.46 (3H, s), 3.40–3.55 (5H, m), 3.55–3.70 (6H, m), 4.49 (2H, s), 5.58 (1H, br s), 7.22–7.36 (4H, m)

EXAMPLE 29

To a solution of 4-[3-(2-hydroxyethyl)-2-methyloxiranyl]-5-methoxy-6-(morpholinocarbonyloxy)-1-oxaspiro[2,5]octane (76.2 mg) in a mixture of toluene (2 ml) and N,N-dimethylformamide (1 ml) was added sodium hydride (20.5 mg) in one portion under ice cooling. The mixture was stirred for half an hour at the same temperature and ethyl bromoacetate (68.5 mg) was added. After stirred for 3 hours at ambient temperature, the reaction mixture was quenched with aqueous saturated ammonium chloride solution (2 ml). The organic layer was washed with brine, dried, and evaporated in vacuo. The residue was purified by column chromatography on silica gel (diethyl ether) to give 4-[3-(2-ethoxycarbonylmethoxyethyl)-2-methyloxiranyl]-5-methoxy-6-(morpholinocarbonyloxy)-1-oxaspiro[2,5]octane (66.9 mg).

Oil

IR (Neat): 1740, 1685, 1450, 1260, 1140 cm⁻¹

NMR (CDCl₃, δ): 1.04–1.15 (1H, m), 1.20 (3H, s), 1.30 (3H, t, J=7 Hz), 1.58–2.14 (6H, m), 2.58 (1H, d, J=4 Hz), 2.80 (1H, dd, J=8 and 5 Hz), 3.00 (1H, d, J=4 Hz), 3.47 (3H, s), 3.32–3.55 (4H, m), 3.55–3.78 (7H, m), 4.10 (2H, s), 4.20 (2H, q, J=7 Hz), 5.58 (1H, br s)

EXAMPLE 30

To a solution of 4-[3-(2-hydroxyethyl)-2-methyloxiranyl]-5-methoxy-6-(morpholinocarbonyloxy)-1-oxaspiro[2,5]octane (11.1 mg) in anhydrous tetrahydrofuran (1 ml) was added sodium hydride (60% oil dispersion, 2.4 mg) in one portion under ice cooling. The mixture was stirred for half an hour at the same temperature and butyl isocyanate (4.5 mg) was added. After stirred for 2 hours at ambient temperature, the solvent was diluted with diethyl ether (2 ml) and washed with water, dried, and evaporated in vacuo. The residue was purified by flash chromatography on silica gel (ethyl acetate) to afford 4-[3-(2-butylcarbamoyloxyethyl)-2-methyloxiranyl]-5-methoxy-6-(morpholinocarbonyloxy)-1-oxaspiro[2,5]octane (10.8 mg).

Oil

IR (Neat) 3350, 1690, 1420, 1240, 1105 cm⁻¹

NMR (CDCl₃, δ): 0.92 (3H, t, J=6 Hz), 1.22 (3H, s), 1.10–1.58 (5H, m), 1.70–2.10 (6H, m), 2.58 (1H, d, J=4 Hz), 2.70 (1H, dd, J=8 and 5 Hz), 2.88 (1H, d, J=4 Hz), 3.18 (2H, dt, J=6 Hz), 3.47 (3H, s), 3.40–3.55 (5H, m), 3.55–3.88 (4H, m), 4.12–4.36 (2H, m), 4.70–4.83 (1H, m), 5.55 (1H, br s)

EXAMPLE 31

The following compound was prepared in a similar manner to that of Example 30.

4-[2-Methyl-3-(2-propylcarbamoyloxyethyl)oxiranyl]-5-methoxy-6-(morpholinocarbonyloxy)-1-oxaspiro[2,5]octane Oil IR (Neat) 3350, 1690, 1420, 1240, 1105 cm⁻¹

NMR (CDCl₃, δ): 0.92 (3H, t, J=6 Hz), 1.20 (3H, s), 1.10–2.10 (9H, m), 2.58 (1H, d, J=4 Hz), 2.70 (1H, dd, J=8 and 5 Hz), 2.88 (1H, d, J=4 Hz), 3.13 (2H, dt, J=6 Hz), 3.47 (3H, s), 3.40–3.55 (5H, m), 3.55–3.88 (4H, m), 4.12–4.36 (2H, m), 4.70–4.83 (1H, m), 5.55 (1H, br s)

EXAMPLE 32

A mixture of 6-cyclohexylcarbamoyloxy-4-[3-(2-hydroxyethyl)-2-methyloxiranyl]-5-methoxy-1-oxaspiro[2,5]-octane (5 mg), acetic anhydride (12 μl), pyridine (11 μl), and 4-dimethylaminopyridine (1 mg) in dichloromethane (1 ml) was stirred for 1.1 hours at ambient temperature. The mixture was diluted with diethyl ether and washed with brine (4×). The organic layer was dried and concentrated in vacuo. The residue was purified by column chromatography on silica gel to yield 4-[3-(2-acetoxyethyl)-2- methyloxiranyl]-6-cyclohexylcarbamoyloxy-5-methoxy-1-oxaspiro[2.5]octane as an oil (3.7 mg).

IR (CHCl$_3$): 3450, 1710 cm$^{-1}$

NMR (CDCl$_3$, δ): 1.00–1.50 (9H, m), 1.20 (3H, s), 1.51–2.17 (8H, m), 2.08 (3H, s), 2.60 (1H, d, J=4 Hz), 2.68 (1H, dd, J=4 Hz and 7 Hz), 2.86 (1H, d, J=4 Hz), 3.45 (3H, s), 3.38–3.55 (1H, m), 3.65 (1H, dd, J=3 Hz and 12 Hz), 4.13–4.36 (2H, m), 4.66 (1H, br d, J=7 Hz), 5.45 (1H, br s)

EXAMPLE 33

A mixture of 6-hydroxy-5-methoxy-4-[2-methyl-3-(3-methyl-2-butenyl)oxiranyl]-1-oxaspiro[2.5]octane (400 mg), p-nitrophenyl chloroformate (570 mg) and pyridine (1.37 ml) in dichloromethane (6 ml) was stirred for 3 hours at ambient temperature and then piperazine (1.0 g) was added thereto. After stirring at ambient temperature for half an hour, the mixture was treated with ethanesulfonyl chloride (183 mg). The reaction mixture was stirred for 15 minutes at 0° C. and for 3 hours at ambient temperature. The resulting mixture was diluted with diethyl ether and washed with 1N HCl, 1N NaOH and brine. The organic layer was dried and concentrated in vacuo to give a crude oil which was purified by silica gel column chromatography to yield 6-[4-(ethanesulfonyl)piperazin-1-ylcarbonyloxy]-5-methoxy-4-[2-methyl-3-(3-methyl-2-butenyl)oxiranyl]-1-oxaspiro[2.5]octane as crystal.

mp: 91°–92° C. (Ether/hexane)

IR (Nujol): 1680, 1455 cm$^{-1}$

NMR (CDCl$_3$, δ): 1.07–1.20 (1H, m), 1.23 (3H, s), 1.40 (3H, t, J=7 Hz), 1.69 (3H, s), 1.78 (3H, s), 1.57–2.50 (6H, m), 2.59 (1H, d, J=4 Hz), 2.58 (1H, t, J=6 Hz), 2.99 (2H, q, J=7 Hz), 3.03 (1H, d, J=4 Hz), 3.10–3.95 (8H, m), 3.49 (3H, s), 3.67 (1H, dd, J=12, 2 Hz), 5.23 (1H, br t, J=7 Hz), 5.62 (1H, br s)

EXAMPLE 34

A mixture of 6-(4,5-dihydroxy-2-hexenoyloxy)-5-methoxy-4-[2-methyl-3-(3-methyl-2-butenyl)oxiranyl]-1-oxaspiro[2.5]octane (which is the same compound as "WF 2015A" and was prepared in the same manner as that described in European Patent Application Publication No. 0314401) (34 mg), acetic anhydride (34 μl), pyridine (30 μl), and 4-dimethylaminopyridine (1 mg) in dichloromethane (0.7 ml) was stirred overnight at ambient temperature. The mixture was diluted with diethyl ether and washed with brine (X3). The organic layer was dried and concentrated in vacuo to yield 6-(4,5-diacetoxy-2-hexenoyloxy)-5-methoxy-4-[2-methyl-3-(3-methyl-2-butenyl)oxiranyl]-1-oxaspiro[2.5]octane (41.7 mg) as a colorless oil.

IR (CHCl$_3$): 1730, 1720 cm$^{-1}$

NMR (CDCl$_3$, δ): 1.23 (3H, s), 1.26 (3H, s), 1.05–1.15 (1H, m), 1.66 (3H, s), 1.74 (3H, s), 1.7–2.5 (6H, m), 2.04 (3H, s), 2.14 (3H, s), 2.57 (1H, d, J=4 Hz), 2.60 (1H, t, J=5, 4 Hz), 3.00 (1H, d, J=4 Hz), 3.42 (3H, s), 3.70 (1H, dd, J=12 Hz and 2 Hz), 5.12 (1H, m), 5.21 (1H, t, J=7 Hz), 5.59 (1H, m), 5.71 (1H, m), 6.10 (1H, dd, J=15 Hz and 1 Hz)

EXAMPLE 35

The following compounds were prepared in a similar manner to that of Example 34.

(1) 6-(4,5-Dibenzyloxy-2-hexenoyloxy)-5-methoxy-4-[2-methyl-3-(3-methyl-2-butenyl)oxiranyl]-1-oxaspiro[2.5]octane mp: 37°–39° C.

IR (CHCl$_3$): 1715, 1260, 1100 cm$^{-1}$

NMR (CDCl$_3$, δ): 1.02–1.18 (1H, m), 1.20 (3H, s), 1.49 (3H, d, J=6 Hz), 1.65 (3H, s), 1.75 (3H, s), 1.81–2.45 (6H, m), 2.55 (1H, d, J=4 Hz), 2.57 (1H, t, J=6 Hz), 2.98 (1H, d, J=6 Hz), 3.43 (3H, s), 3.70 (1H, dd, J=3 Hz and 10 Hz), 5.68 (1H, br t, J=8 Hz), 5.43–5.57 (1H, m), 5.70 (1H, br s), 5.95 (1H, br s), 6.22 (1H, dd, J=1 Hz and 15 Hz), 7.07 (1H, dd, J=5 Hz and 15 Hz), 7.35–7.68 (6H, m), 7.93–8.12 (4H, m)

(2) 6-(4-Acetoxycrotonoyloxy)-5-methoxy-4-[2-methyl-3-(3-methyl-2-butenyl)oxiranyl]-1-oxaspiro[2.5]octane Oil IR (CHCl$_3$): 1730, 1715 cm$^{-1}$ NMR (CDCl$_3$, δ): 1.03–1.18 (1H, m), 1.22 (3H, s), 1.66 (3H, s), 1.75 (3H, s), 1.84–2.50 (6H, m), 2.15 (3H, s), 2.56 (1H, d, J=4 Hz), 2.60 (1H, t, J=6 Hz), 3.00 (1H, d, J=4 Hz), 3.44 (3H, s), 3.69 (1H, dd, J=2 Hz and 12 Hz), 4.71–4.78 (2H, m), 5.22 (1H, br t, J=7 Hz), 5.70 (1H, br s), 6.09 (1H, d, J=16 Hz), 6.94 (1H, td, J=5 Hz and 16 Hz)

EXAMPLE 36

To a mixture of 6-carboxymethoxy-5-methoxy-4-[2-methyl-3-(3-methyl-2-butenyl)oxiranyl]-1-oxaspiro[2.5]-octane (9.0 mg), triethylamine (2.5 mg), and 4-dimethylaminopyridine (0.6 mg) in dichloromethane (1 ml) was added dropwise tert-butylcarbonyl chloride (3.5 mg) under ice cooling. The mixture was stirred for half an hour at ambient temperature and propylamine (2.9 mg) was added. After stirred for 2 hours at the same temperature, the solution was washed with water, aqueous HCl solution, saturated aqueous NaHCO$_3$ solution, and brine successively. The organic layer was dried and concentrated in vacuo. The residue was purified by flash chromatography on silica gel (diethyl ether-ethyl acetate =1-1) to give 5-methoxy-4-[2-methyl-3-(3-methyl-2-butenyl)oxiranyl]-6-propylcarbamoylmethoxy-1-oxaspiro[2.5]octane (7.6 mg).

Oil

IR (Neat): 3350, 1660, 1540, 1440, 1380, 1110 cm$^{-1}$

NMR (CDCl$_3$, δ): 0.92 (3H, t, J=7 Hz), 0.95–1.06 (1H, m), 1.22 (3H, s), 1.45–1.70 (2H, m), 1.65 (3H, s), 1.73 (3H, s), 1.90–2.46 (6H, m), 2.55 (1H, d, J=4 Hz), 2.58 (1H, t, J=8 Hz), 2.96 (1H, d, J=4 Hz), 3.08–3.42 (2H, m), 3.48 (3H, s), 3.60 (1H, dd, J=11 and 3 Hz), 3.88 (1H, d, J=15 Hz), 3.95 (1H, br s), 4.14 (1H, d, J=15 Hz), 5.22 (1H, br t, J=8 Hz), 7.50 (1H, br s)

EXAMPLE 37

The following compound was prepared in a similar manner to that of Example 9.

6-(3-Carboxypropylcarbamoyloxy)-5-methoxy-4-[2-methyl-3-(3-methyl-2-butenyl)oxiranyl]-1-oxaspiro[2.5] octane.

Oil

IR (CHCl$_3$) 3440, 3100, 1710, 1100 cm$^{-1}$

NMR (CDCl$_3$, δ): 0.95–1.12 (1H, m), 1.21 (3H, s), 1.66 (3H, s), 1.75 (3H, s), 1.70–2.52 (10H, m), 2.53 (1H, d, J=7 Hz), 2.76 (1H, t, J=7 Hz), 2.94 (1H, d, J=6 Hz), 2.96–3.18 (2H, m), 3.43 (3H, s), 3.58 (1H, dd, J=14, 2 Hz), 4.92–5.06 (1H, m), 5.18 (1H, br t, J=7 Hz), 5.47 (1H, br s)

EXAMPLE 38

To a solution of 5-methoxy-4-[(2-methyl-3-(3-methyl-2-butenyl)oxiranyl]-6-methylcarbamoyloxy-1-oxaspiro[2.5] octane (382 mg) in a mixture of methanol (1.0 ml) and dichloromethane (10 ml) was passed through ozone for 5 minutes at –78° C. After bubbling of nitrogen, solvent was removed and methanol (5 ml) was added to this mixture.

This solution was cooled to 0° C. and sodium borohydride (20 mg) was then added. The reaction mixture was stirred for 30 minutes at 0° C., and then water (3 ml) was added. The reaction mixture was diluted with ethyl acetate. The ethyl acetate solution was washed with water and brine and then dried over MgSO$_4$. Evaporation of solvents in vacuo gave essentially pure alcohol, 4-[3-(2-hydroxyethyl)-2-methyloxiranyl]-5-methoxy-6-methylcarbamoyl-1-oxaspiro[2.5]octane (300 mg), which was used in the next step without further purification. The crude alcohol (29 mg) was dissolved in tetrahydrofuran (2 ml) at 0° C. and sodium hydride (60% oil, 20 mg) was then added. The reaction mixture was stirred for 30 minutes and methyl isocyanate (11 μl) was added. The mixture was stirred for 6 hours at ambient temperature. The solution was recooled (0° C.) and diluted with ether (10 ml) and water (1 ml) was cautiously added. The extracted ether solution was washed with brine and dried (MgSO$_4$). The solvents were removed in vacuo, and the resulting residue was purified by thin layer chromatography to provide 5-methoxy-4-[2-methyl-3-(2-methylcarbamoyloxyethyl)oxiranyl]-6-methylcarbamoyloxy-1-oxaspiro[2.5]octane (4.4 mg).

NMR (CDCl$_3$, δ): 1.05–1.23 (1H, m), 1.20 (3H, s), 1.73–2.12 (6H, m), 2.59 (1H, d, J=4 Hz), 2.71 (1H, dd, J=8, 5 Hz), 2.78 (3H, d, J=5 Hz), 2.79 (3H, d, J=5 Hz), 2.87 (1H, d, J=4 Hz), 3.46 (3H, s), 3.65 (1H, dd, J=12, 3 Hz), 4.15–4.49 (2H, m), 4.64–4.83 (2H, br s), 5.43–5.53 (1H, br s)

We claim:
1. An oxaspiro[2.5]octane derivative of the formula:

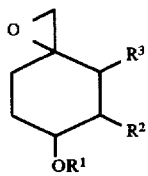

(I)

wherein
R$^1$ is carbamoyl;
lower alkylcarbamoyl;
hydroxy (lower)alkylcarbamoyl;
lower alkoxy(lower)alkylcarbamoyl;
lower alkylthio(lower)alkylcarbamoyl;
lower alkoxycarbonyl(lower)alkylcarbamoyl;
lower alkylcarbamoyloxy(lower)alkylcarbamoyl;
di(lower)alkylcarbamoyl;
N-[hydroxy(lower)alkyl](lower)alkylcarbamoyl;
N-[hydroxy(lower)alkyl](lower)alkylcarbamoyloxy(lower)alkylcarbamoyl;
lower alkylcarbamoyloxy(lower)alkenoyl;
N-[heterocycliccarbonyloxy(lower)alkyl](lower)alkylcarbamoyl;
cyclo(lower)alkylcarbamoyl;
arylcarbamoyl;
haloarylcarbamoyl;
protected carbamoyl;
lower alkylthiocarbamoyl;
heterocycliccarbamoyl;
ar(lower)alkenoyl;
lower alkoxycarbonyl;
heterocycliccarbonyl which may have lower alkyl, hydroxy(lower) alkyl, lower alkoxy(lower)alkyl or lower alkoxycarbonyl;
lower alkyl;
carboxy(lower)alkyl;
protected carboxy(lower)alkyl;
ar(lower)alkyl which may have halogen or lower alkoxy;
heterocyclic(lower)alkyl;
lower alkylcarbamoyl(lower)alkyl;
hydroxy(lower)alkenoyl;
acyloxy(lower)alkenoyl; or
diacyloxy(lower)alkenoyl;

R$^2$ is lower alkoxy and
R$^3$ is

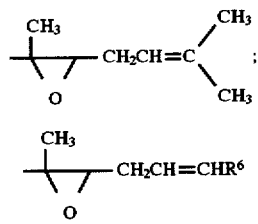

wherein R$^6$ is a protected carboxy;

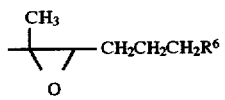

wherein R$^6$ is a protected carboxy;

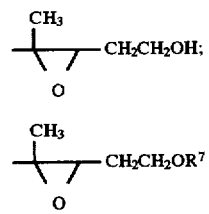

wherein R$^7$ is a protected carboxy(lower)alkyl or ar(lower)alkyl which may have halogen; or

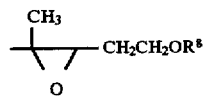

wherein R$^8$ is acyl, wherein aryl is selected from the group consisting of phenyl, tolyl, xylyl and naphthyl, wherein heterocyclic is selected from the group consisting of pyridyl, pyrrolidyl, piperidyl, piperazinyl, 2-oxopyrrolidyl, morpholinyl, thiomorpholinyl and quinolyl, wherein acyl is selected from the group consisting of lower alkanoyl, aroyl and lower alkanesulfonyl, or pharmaceutically acceptable salt thereof.

2. The compound of claim 1, wherein

R$^1$ is lower alkylcarbamoyl,
R$^2$ is lower alkoxy and $R^3$ is

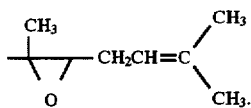

3. The compound of claim 2, wherein
$R^1$ is methylcarbamoyl,
$R^2$ is methoxy and
$R^3$ is the same as defined in claim 2.

4. The compound of claim 1, wherein said protected carboxy is esterified carboxy.

5. The compound of claim 1, wherein said protected carbamoyl is trichloroacetyl carbamoyl.

6. An angiogenesis inhibitory pharmaceutical composition, which comprises, as an active ingredient, an effective amount of the oxaspiro[2.5]octane derivative (I) of claim 1 or pharmaceutically acceptable salt thereof and pharmaceutically acceptable carrier(s).

7. A method of inhibiting angiogenesis in a solid tumor in a subject in need thereof, which comprises administering an effective amount of the oxaspiro[2.5]octane derivative (I) of claim 1 or pharmaceutically acceptable salt thereof to said subject.

8. 5-Methoxy-4-[2-methyl-3-(3-methyl-2-butenyl) oxiranyl]-6-phenylcarbamoyloxy-1-oxaspiro[2.5]octane.

9. 6-Ethylcarbamoyloxy-5-methoxy-4-[2-methyl-3-(3-methyl-2-butenyl)oxiranyl]-1-oxaspiro[2.5]octane.

10. 6-Isopropylcarbamoyloxy-5-methoxy-4-[2-methyl-3-(3-methyl-2-butenyl)oxiranyl]-1-oxaspiro[2.5]octane.

11. 6-Cyclohexylcarbamoyloxy-5-methoxy-4-[2-methyl-3-(3-methyl-2-butenyl)oxiranyl]-1-oxaspiro[2.5]octane.

12. 6-(4-Chlorophenylcarbamoyloxy)-5-methoxy-4-[2-methyl-3-(3-methyl-2-butenyl)oxiranyl]-1-oxaspiro[2.5]octane.

13. 5-Methoxy-4-[2-methyl-3-(3-methyl-2-butenyl) oxiranyl]-6-trichloroacetylcarbamoyloxy-1-oxaspiro[2.5] octane.

14. 6-Carbamoyloxy-5-methoxy-4-[2-methyl-3-(3-methyl-2-butenyl)oxiranyl]-1-oxaspiro[2.5]octane.

15. A method of inhibiting angiogenesis in a solid tumor in a subject in need thereof, which comprises administering an effective amount of 6-carbamoyloxy-5-methoxy-4-[2-methyl-3-(3-methyl-2-butenyl)oxiranyl]-1-oxaspiro[2.5] octane to said subject.

16. A method of inhibiting angiogenesis in a solid tumor in a subject in need thereof, which comprising administering an effective amount of 6-methylcarbamoyloxy-5-methoxy-4-[2-methyl-3-(3-methyl-2-butenyl)oxiranyl]-1-oxaspiro[2.5]octane to said subject.

* * * * *